US012307688B2

(12) United States Patent
Igarashi et al.

(10) Patent No.: US 12,307,688 B2
(45) Date of Patent: May 20, 2025

(54) ANALYSIS APPARATUS AND ULTRASOUND DIAGNOSIS APPARATUS

(71) Applicant: Canon Medical Systems Corporation, Otawara (JP)

(72) Inventors: Yu Igarashi, Utsunomiya (JP); Masaki Watanabe, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 528 days.

(21) Appl. No.: 16/798,665

(22) Filed: Feb. 24, 2020

(65) Prior Publication Data

US 2020/0273181 A1 Aug. 27, 2020

(30) Foreign Application Priority Data

Feb. 26, 2019 (JP) .................................. 2019-032948
Feb. 20, 2020 (JP) .................................. 2020-027454

(51) Int. Cl.
*G06T 7/246* (2017.01)
*A61B 8/00* (2006.01)
*A61B 8/08* (2006.01)

(52) U.S. Cl.
CPC ................ *G06T 7/248* (2017.01); *A61B 8/08* (2013.01); *A61B 8/463* (2013.01); *A61B 8/486* (2013.01);
(Continued)

(58) Field of Classification Search
CPC ........... G06T 7/248; G06T 2207/10132; G06T 2207/10016; G06T 2207/30101;
(Continued)

(56) References Cited

U.S. PATENT DOCUMENTS 5,241,473 A * 8/1993 Ishihara .................... G06T 5/50
600/443
5,619,995 A * 4/1997 Lobodzinski .......... G16H 40/67
600/301
(Continued)

FOREIGN PATENT DOCUMENTS

JP 9-16776 A 1/1997
JP 2007-330764 A 12/2007
(Continued)

OTHER PUBLICATIONS

JP 2018015155 Translation (Year: 2018).*
(Continued)

*Primary Examiner* — Adil Partap S Virk
(74) *Attorney, Agent, or Firm* — Oblon, McClelland, Maier & Neustadt, L.L.P.

(57) ABSTRACT

According to one embodiment, the analysis apparatus includes processing circuitry. The processing circuitry acquires a plurality of medical images respectively corresponding to a plurality of consecutive frames, generates first position data and second position data indicating positions of a moving object in a subject for a first medical image corresponding to a first frame and a second medical image corresponding to a second frame that is two or more frames prior to the first frame of the plurality of medical images, calculates a vector representing a movement of the moving object based on the first position data and the second position data, and generates display image data having a shape representing the vector.

10 Claims, 17 Drawing Sheets

(52) U.S. Cl.
CPC .......... *A61B 8/5207* (2013.01); *A61B 8/5223* (2013.01); *A61B 8/5246* (2013.01); *G06T 2207/10132* (2013.01)

(58) Field of Classification Search
CPC ........... A61B 8/08; A61B 8/463; A61B 8/486; A61B 8/5207; A61B 8/5223; A61B 8/5246; A61B 8/488; A61B 8/5276; A61B 8/06; A61B 8/0833; A61B 8/481
See application file for complete search history.

(56) References Cited

U.S. PATENT DOCUMENTS

| | | | | |
|---|---|---|---|---|
| 5,873,830 | A * | 2/1999 | Hossack | G01S 7/52085 600/447 |
| 10,107,909 | B2 * | 10/2018 | Taki | A61B 8/06 |
| 10,265,053 | B2 * | 4/2019 | Yoshida | A61B 8/5276 |
| 10,537,310 | B2 * | 1/2020 | Tanaka | A61B 8/463 |
| 10,575,827 | B2 * | 3/2020 | Shikama | A61B 8/5276 |
| 11,259,784 | B2 * | 3/2022 | Du | A61B 8/461 |
| 2001/0024516 | A1 * | 9/2001 | Yoshioka | G01S 7/52073 382/128 |
| 2002/0183619 | A1 * | 12/2002 | Hayasaka | G01S 7/5205 600/443 |
| 2003/0153823 | A1 * | 8/2003 | Geiser | G06T 7/0012 600/407 |
| 2004/0034304 | A1 * | 2/2004 | Sumi | G01S 7/52042 600/439 |
| 2004/0215076 | A1 * | 10/2004 | Kamiyama | A61B 8/481 600/443 |
| 2005/0259739 | A1 * | 11/2005 | Nakamura | H04N 5/145 348/E7.013 |
| 2008/0267482 | A1 * | 10/2008 | Abe | A61B 8/5246 382/131 |
| 2009/0169080 | A1 * | 7/2009 | Noordhoek | G06T 5/73 382/131 |
| 2010/0069757 | A1 * | 3/2010 | Yoshikawa | A61B 5/02007 600/454 |
| 2012/0027282 | A1 * | 2/2012 | Yoshikawa | A61B 8/13 382/131 |
| 2013/0150717 | A1 * | 6/2013 | Sato | A61B 8/466 600/443 |
| 2014/0088426 | A1 * | 3/2014 | Miyachi | A61B 8/5207 600/443 |
| 2014/0119610 | A1 * | 5/2014 | Funaya | A61B 8/469 382/107 |
| 2015/0005637 | A1 * | 1/2015 | Stegman | A61B 8/5223 600/449 |
| 2015/0094580 | A1 * | 4/2015 | Waki | A61B 8/42 382/131 |
| 2015/0141832 | A1 * | 5/2015 | Yu | A61B 8/488 600/455 |
| 2015/0327838 | A1 * | 11/2015 | Francis | A61B 8/4433 600/459 |
| 2018/0199998 | A1 * | 7/2018 | Chen | G06F 3/04815 |
| 2019/0216439 | A1 * | 7/2019 | Somphone | A61B 8/469 |
| 2019/0314000 | A1 * | 10/2019 | Du | A61B 8/5246 |
| 2020/0126219 | A1 * | 4/2020 | Wang | A61B 8/463 |

FOREIGN PATENT DOCUMENTS

| | | |
|---|---|---|
| JP | 2016-153005 A | 8/2016 |
| JP | 2017-38837 A | 2/2017 |
| JP | 2018-15155 A | 2/2018 |
| JP | 2018015155 A * | 2/2018 |

OTHER PUBLICATIONS

Mikla et al., "Medical Imaging Technology" (Year: 2014).*
Japanese Office Action issued Jun. 13, 2023 in Japanese Patent Application No. 2020-027454, 3 pages.

* cited by examiner

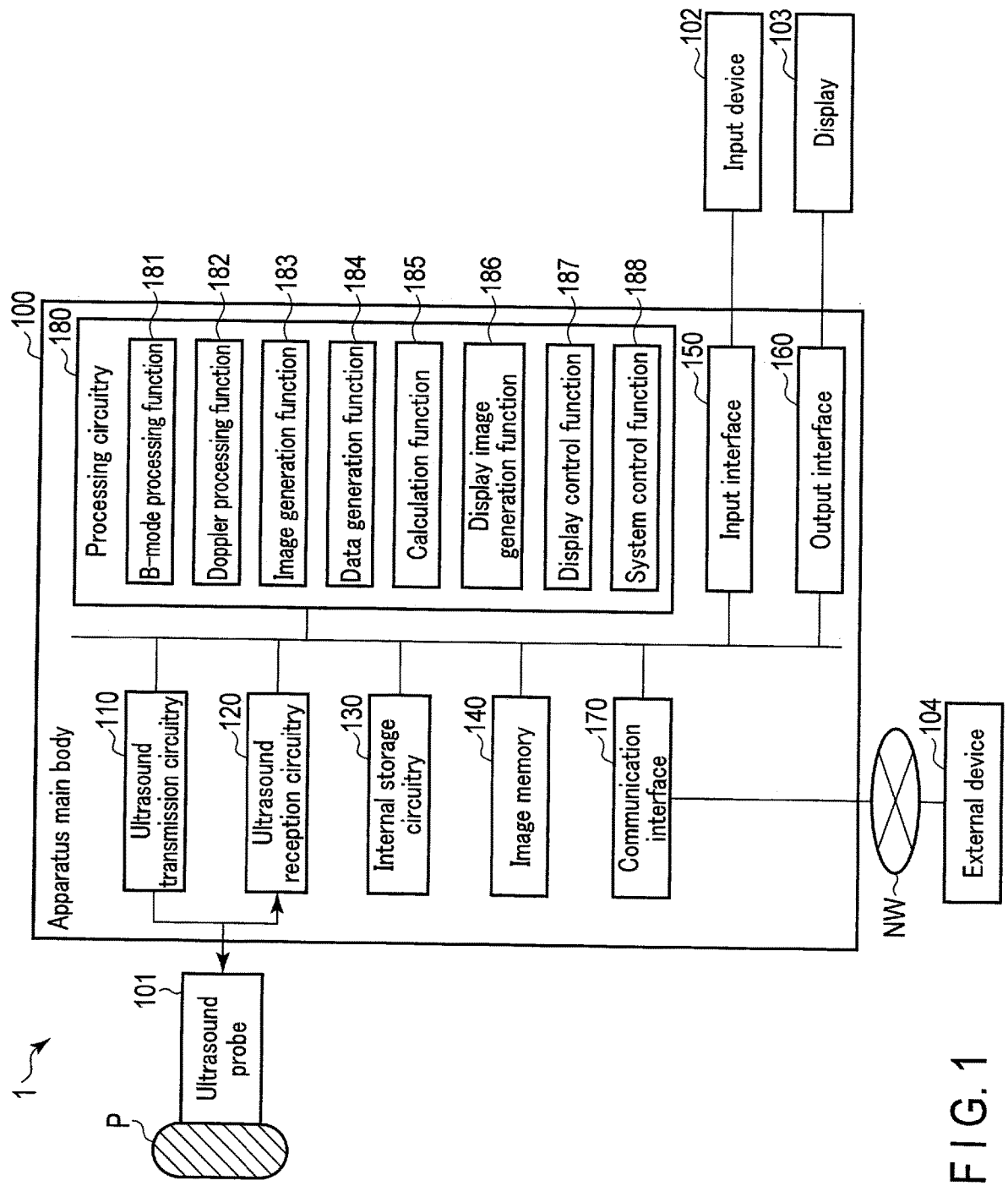
F I G. 1

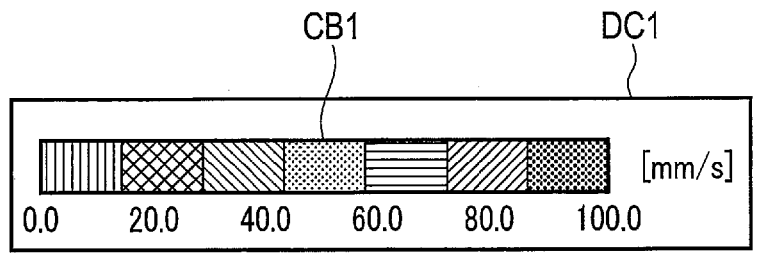
F I G. 5
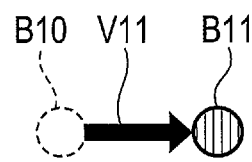
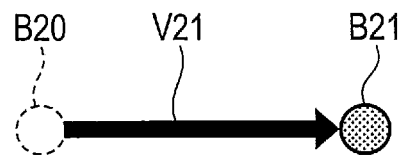
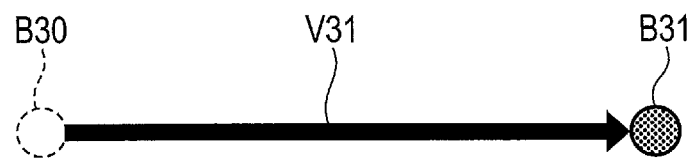
F I G. 6
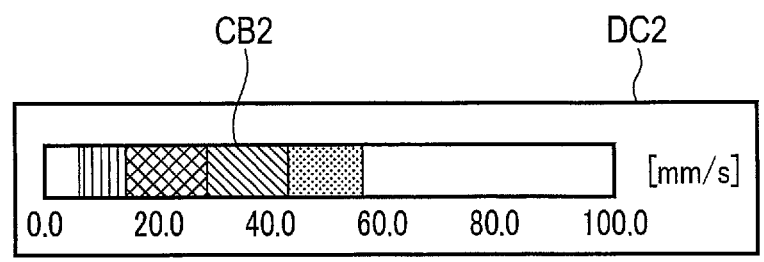
F I G. 7

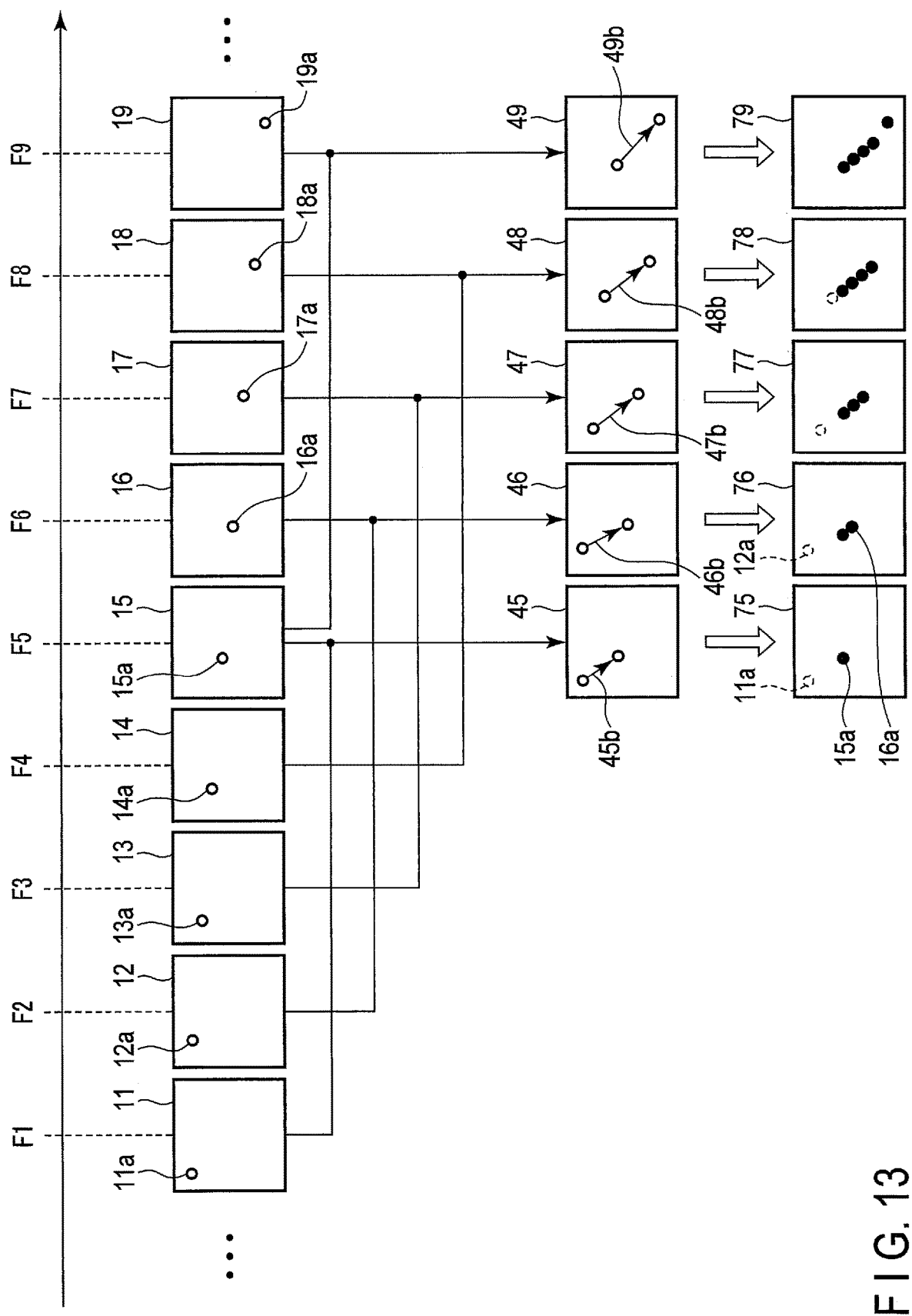
F I G. 13

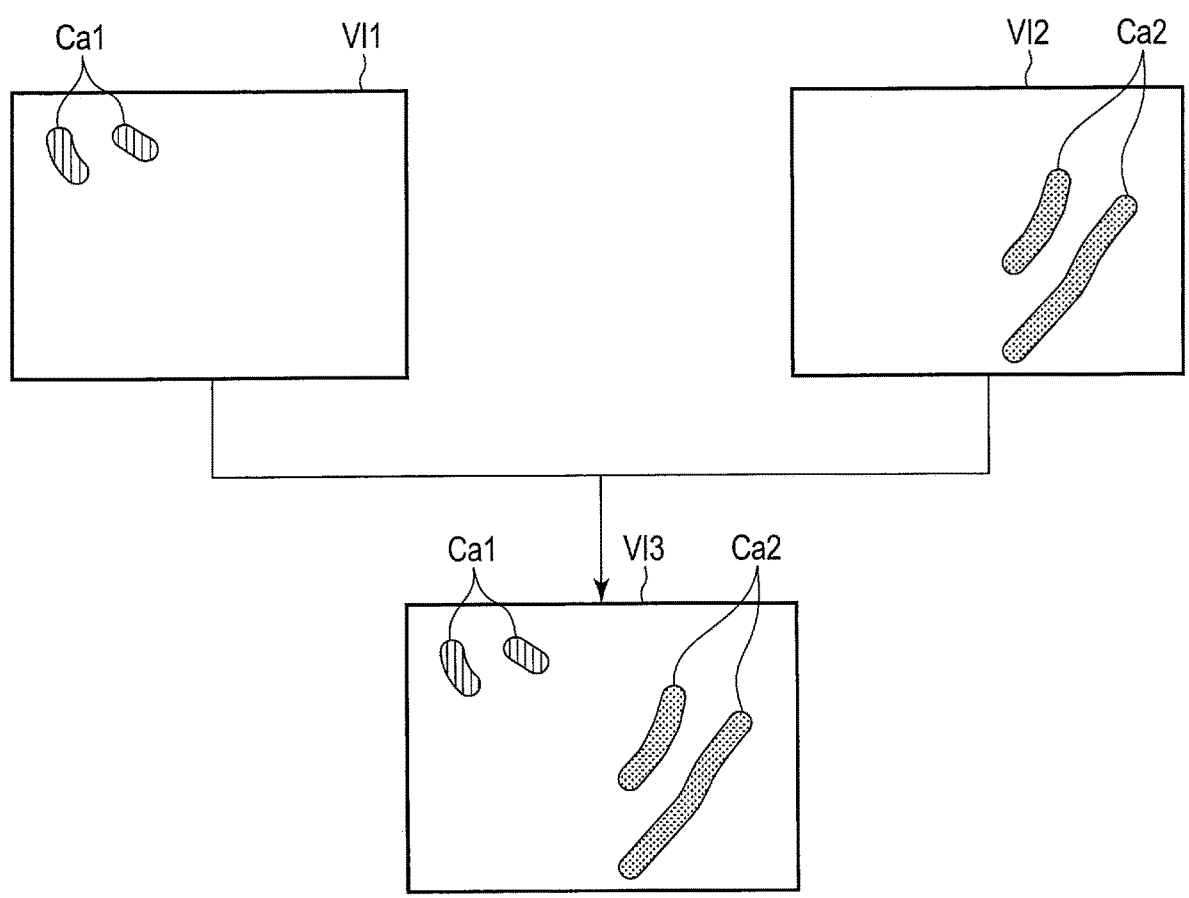
F I G. 17

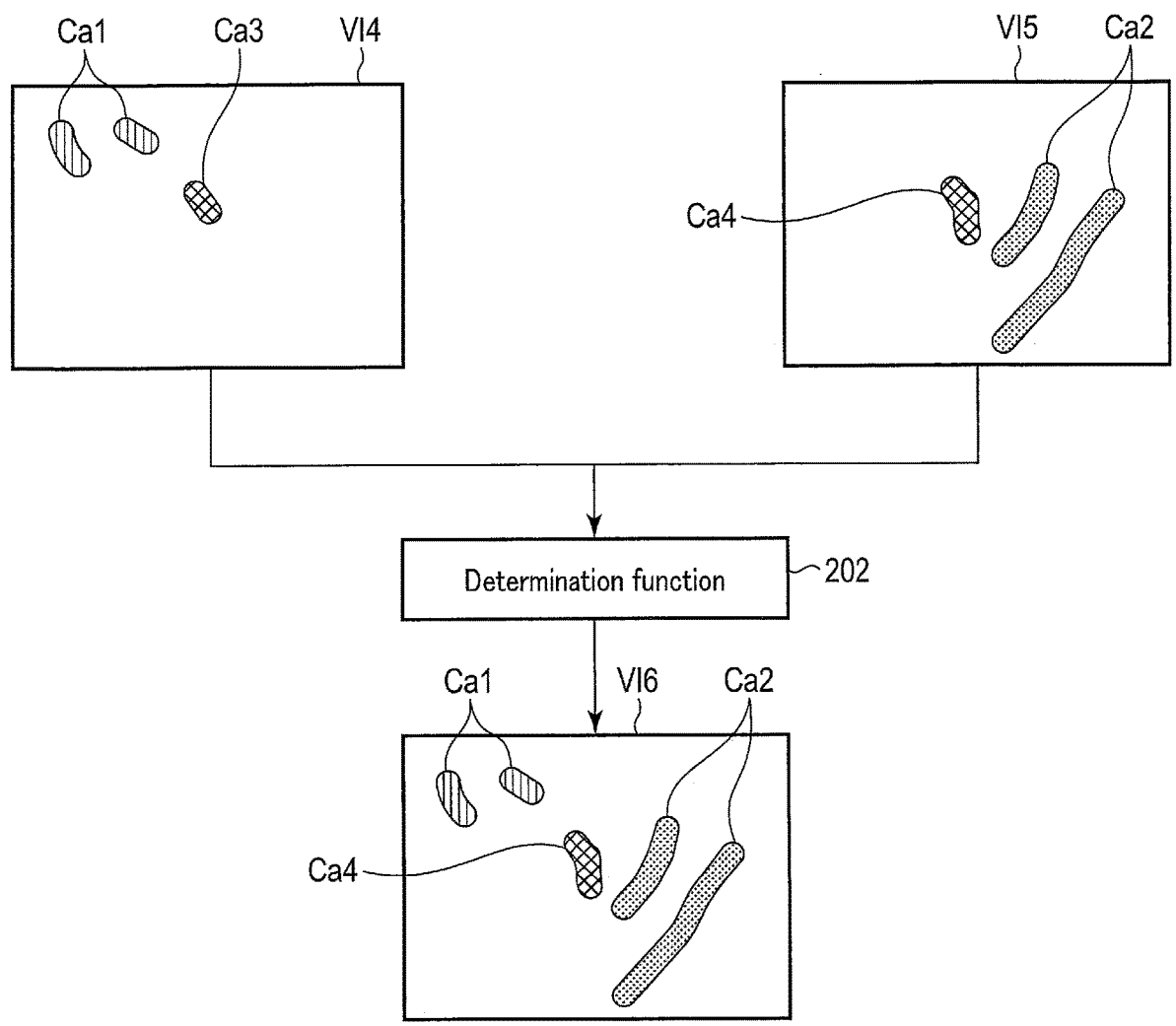
F I G. 21

ANALYSIS APPARATUS AND ULTRASOUND DIAGNOSIS APPARATUS

CROSS-REFERENCE TO RELATED APPLICATIONS

This application is based upon and claims the benefit of priority from Japanese Patent Applications No. 2019-32948, filed Feb. 26, 2019; and No. 2020-27454, filed Feb. 20, 2020; the entire contents of both of which are incorporated herein by reference.

FIELD

Embodiments described herein relate generally to an analysis apparatus, and an ultrasound diagnosis apparatus.

BACKGROUND

Conventional ultrasound diagnosis apparatuses use a contrast echo method called Contrast Harmonic Imaging (CHI). In the contrast echo method, a contrast agent is injected through a vein to inspect the heart, liver, etc., to create an image. Many contrast agents for use in the contrast echo method use microbubbles as reflection sources. The contrast echo method enables clear depiction of a blood vessel of a subject or depiction of a flow of the contrast agent in the blood vessel.

For example, to depict a flow of the contrast agent in the blood vessel by tracking a movement of the contrast agent in each frame, the ultrasound diagnosis apparatus sets a frame rate in accordance with the speed of the bloodstream. However, when using a contrast agent which moves a little between frames, displacement of the contrast agent cannot be detected and tracking of the contrast agent cannot be stable.

BRIEF DESCRIPTION OF THE DRAWINGS

FIG. 1 is a block diagram showing a configuration example of an ultrasound diagnosis apparatus according to a first embodiment.

FIG. 5 is a diagram for explaining a display example of a color bar according to the first embodiment.

FIG. 6 is a diagram for explaining a display example of bubbles in display image data according to the first embodiment.

FIG. 7 is a diagram for explaining a color bar related to display conditions in normal time according to the first embodiment.

FIG. 13 is a diagram for explaining another generation example of display image data in a case of carrying out the decimation processing according to the first embodiment.

FIG. 17 is a diagram for explaining processing of a display image generation function according to the second embodiment.

FIG. 21 is a diagram for explaining processing of a determination function and a display image generation function according to the third embodiment.

DETAILED DESCRIPTION

Figure 2:
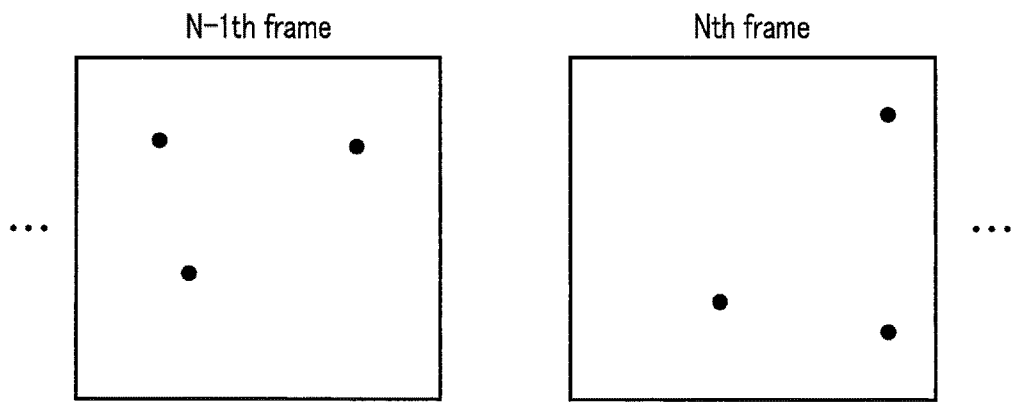
FIG. 2 is a diagram for explaining processing of a data generation function according to the first embodiment.

In general, according to one embodiment, the analysis apparatus includes processing circuitry. The processing circuitry acquires a plurality of medical images respectively corresponding to a plurality of consecutive frames, generates first moving-object position data and second moving-object position data indicating positions of a moving object in a subject respectively for a first medical image and a second medical image of the plurality of medical images, the first medical image corresponding to a first frame, the second medical image corresponding to a second frame that is two or more frames prior to the first frame, calculates a vector representing a movement of the moving object based on the first moving-object position data and the second moving-object position data, and generates display image data having a shape representing the vector.

Hereinafter, embodiments of the ultrasound diagnosis apparatus and the analysis apparatus will be explained in detail with reference to the accompanying drawings.

First Embodiment

FIG. 1 is a block diagram showing a configuration example of an ultrasonic diagnostic apparatus 1 according to the first embodiment. The ultrasound diagnosis apparatus 1 includes an apparatus main body 100 and an ultrasound probe 101. The apparatus main body 100 is connected to an input device 102 and a display 103. The apparatus main body 100 is connected to an external device 104 via a network NW.

The ultrasound probe 101 executes ultrasound scanning in a scan area of a living body P, which is a subject, under the control of, for example, the apparatus main body 100. The ultrasound probe 101 includes, for example, a plurality of piezoelectric oscillators, a matching layer provided in each piezoelectric oscillator, and a backing member for preventing backward propagation of ultrasound from the piezoelectric oscillators. The ultrasound probe 101 is, for example, a one-dimensional array linear probe in which a plurality of ultrasound transducers are arranged in a predetermined direction. The ultrasound probe 101 is detachably connected to the apparatus main body 100. The ultrasound probe 101 may be provided with a button which is to be depressed in an offset process or in case of freezing of ultrasound images.

The piezoelectric oscillators generate ultrasound waves in response to a drive signal supplied from ultrasound transmission circuitry 110 included in the apparatus main body 100. Ultrasound waves are thereby transmitted from the ultrasound probe 101 to the living body P. When ultrasound waves are transmitted from the ultrasound probe 101 to the living body P, the transmitted ultrasound waves are sequentially reflected on the acoustic impedance discontinuous surface of the body tissue of the living body P, and are received as reflection wave signals by piezoelectric elements. The amplitude of a received reflection wave signal depends on the difference in acoustic impedance on the discontinuous surface from which the ultrasound wave is reflected. If the transmitted ultrasound pulse is reflected from the surface of moving bloodstream or cardiac wall, the frequency of the resultant reflection wave signal will be shifted due to the Doppler effect with the shift depending on the velocity component in the ultrasound transmission direction of the moving object. The ultrasound probe 101 receives the reflection wave signal from the living body P, and converts it into an electric signal.

FIG. 1 merely illustrates a connection relationship between the ultrasound probe 101 used for ultrasound scanning and the apparatus main body 100. However, the apparatus main body 100 is capable of connecting a plurality of ultrasound probes. The connected plurality of ultrasound probes can be switched discretionarily to be selected for use in ultrasound scanning.

The apparatus main body 100 is an apparatus that generates an ultrasound image based on the reflection wave signal received by the ultrasound probe 101. The apparatus main body 100 includes ultrasound transmission circuitry 110, ultrasound reception circuitry 120, internal storage circuitry 130, an image memory 140, an input interface 150, an output interface 160, a communication interface 170, and processing circuitry 180.

The ultrasound transmission circuitry 110 is a processor that supplies a drive signal to the ultrasound probe 101. The ultrasound transmission circuitry 110 is realized by, for example, a trigger generation circuit, a delay circuit, and a pulser circuit. The trigger generation circuit repeatedly generates rate pulses for forming transmission ultrasound waves at a predetermined rate frequency. The delay circuit gives a delay time for each piezoelectric oscillator to each rate pulse generated by the trigger generation circuit. This delay time is required to converge the ultrasound wave generated from the ultrasound probe into a beam and determine the transmission directivity. The pulser circuit applies a drive signal (drive pulse) to a plurality of ultrasound transducers of the ultrasound probe 101 at the timing based on a rate pulse. By varying the delay time provided to each rate pulse by the delay circuit, the transmission direction from the piezoelectric oscillator surface can be freely adjusted.

The ultrasound transmission circuitry 110 is capable of changing the output intensity of ultrasound waves in accordance with a drive signal. In the ultrasound diagnosis apparatus, the influence of attenuation of ultrasound waves in the living body P can be reduced by increasing the output intensity of the ultrasound waves. By reducing the influence of attenuation of ultrasound waves, the ultrasound diagnosis apparatus can obtain a reflection wave signal with a large S/N ratio at the time of reception.

Generally, when an ultrasound wave propagates through the living body P, the intensity of vibration of the ultrasound wave corresponding to the output intensity (also referred to as acoustic power) is reduced. The acoustic power is reduced by absorption, scattering, reflection, etc. The degree of reduction of the acoustic power depends on the frequency of the ultrasound wave and the distance in radiation direction of the ultrasound wave. For example, the degree of power reduction is increased by increasing the frequency of the ultrasound wave. The degree of power reduction is also increased as the distance in radiation direction of the ultrasound wave is increased.

The ultrasound reception circuitry 120 is a processor that performs various processes on the reflection wave signal received by the ultrasound probe 101 and thereby generates a reception signal. The ultrasound reception circuitry 120 generates a reception signal corresponding to a low acoustic pressure signal of the ultrasound wave obtained by the ultrasound probe 101 to generate a reception signal. Specifically, the ultrasound reception circuitry 120 is realized by, for example, a preamplifier, an A/D converter, a demodulator, a beam former, etc. The preamplifier performs gain correction processing by amplifying the reflection wave signal received by the ultrasound probe 101 for each channel. The A/D converter converts the gain-corrected reflection wave signal into a digital signal. The demodulator demodulates a digital signal. The beam former, for example, provides the demodulated digital signal with a delay time necessary for determining a reception directivity, and adds a plurality of digital signals each given the delay time. By the addition process of the beam former, a reception signal with an enhanced reflected component in a direction corresponding to the reception directivity is generated.

The internal storage circuitry 130 includes, for example, a magnetic or optical storage medium, or a processor-readable storage medium such as a semiconductor memory. The internal storage circuitry 130 stores therein a program, various data or the like for realizing ultrasound transmission/reception. The program and data may be pre-stored in the internal storage circuitry 130.
Alternatively, the program and data may be stored and distributed in a non-transitory storage medium, read from the non-transitory storage medium and installed in the internal storage circuitry 130. The internal storage circuitry 130 stores B-mode image data and contrast image data generated at the processing circuitry 180, in accordance with an operation that is input via the input interface 150. The internal storage circuitry 130 can transfer the stored data to the external device 104 or the like via the communication interface 170.

The internal storage circuitry 130 may be a drive etc. which reads and writes various types of information to and from a portable storage medium, such as a CD-ROM drive, a DVD drive, and a flash memory. The internal storage circuitry 130 may write the stored data onto a portable storage medium to store the data into the external device 104 by way of the portable storage medium.

The image memory 140 includes, for example, a storage medium which is readable by a processor, such as a magnetic or optical storage medium, or a semiconductor memory. The image memory 140 stores image data items corresponding to a plurality of frames immediately before a freeze operation input via the input interface 150. The image data stored in the image memory 140 is, for example, continuously displayed (cine-displayed).

The internal storage circuitry 130 and the image memory 140 are not necessarily implemented by independent storage devices. The internal storage circuitry 130 and the image memory 140 may be implemented by a single storage device. The internal storage circuitry 130 and the image memory 140 may each be implemented by a plurality of storage devices.

The input interface 150 receives various instructions from an operator through the input device 102. The input device 102 is, for example, a mouse, a keyboard, a panel switch, a slider switch, a trackball, a rotary encoder, an operation panel, or a touch command screen (TCS). The input interface 150 is coupled to the processing circuitry 180 via a bus, for example, so that it can convert an operation instruction that is input by the operator, to an electric signal, and output the electric signal to the processing circuitry 180. The input interface 150 is not limited to a component that is coupled to a physical operation component, such as a mouse and keyboard. For example, the input interface may include circuitry which receives an electric signal corresponding to an operation instruction input from an external input device provided independently from the ultrasound diagnosis apparatus 1, and outputs the electric signal to the processing circuitry 180.

The output interface 160 is an interface, for example, to output an electric signal from the processing circuitry 180 to the display 103. The display 103 may be any type of display, such as a liquid crystal display, an organic EL display, an LED display, a plasma display, and a CRT display. The output interface 160 is connected to the processing circuitry 180 via, for example, a bus, and outputs the electric signal from the processing circuitry 180 to the display.

The communication interface 170 is connected to the external device 104 via, for example, the network NW, and performs data communication with the external device 104.

The processing circuitry 180 is a processor acting as a nerve center of the ultrasound diagnosis apparatus 1, for example. The processing circuitry 180 executes the programs stored in the internal storage circuitry 130, thereby realizing the functions corresponding to the programs. The processing circuitry 180 includes, for example, a B-mode processing function 181, a Doppler processing function 182, an image generation function 183 (image generator), a data generation function 184 (data generator), a calculation function 185 (calculator), a display image generation function 186 (display image generator), a display control function 187 (display controller), and a system control function 188.

The B-mode processing function 181 is a function of generating B-mode data based on the reception signal received from the ultrasound reception circuitry 120. In the B-mode processing function 181, the processing circuitry 180 performs an envelope detection process, a logarithmic compression process and the like on, for example, the reception signal received from the ultrasound reception circuitry 120 to generate data (B-mode data) that expresses signal intensity by brightness. The generated B-mode data is stored in a raw data memory (not shown in the drawings) as B-mode raw data on a two-dimensional ultrasound scan line (raster).

Furthermore, the processing circuitry 180 can execute the contrast echo method, for example, contrast harmonic imaging (CHI) by the B-mode processing function 181. Specifically, the processing circuitry 180 can separate reflection wave data (a harmonic component or a subharmonic component) of the subject P in which the contrast agent has been injected, and reflection wave data (a fundamental wave component) whose reflection source is a living tissue in the subject P. As a result, the processing circuitry 180 can extract a harmonic component or a subharmonic component from the reflection wave data of the subject P, thereby generating B-mode data to generate contrast image data.

The B-mode data to generate contrast image data is data expressing a signal intensity of the reflection wave, whose reflection source is the contrast agent, by brightness. The processing circuitry 180 can extract a fundamental wave component from the reflection wave data of the subject P, thereby generating B-mode data to generate living tissue image data.

When performing the CHI, the processing circuitry 180 can extract a harmonic component by a method other than the above-described method using the filtering process. In the harmonic imaging, an amplitude modulation (AM) method, a phase modulation (PM) method, or an imaging method called an AMPM method, which is a combination of the AM method and the PM method, is performed.

With the AM method, the PM method, or the AMPM method, ultrasound transmission is performed more than once for a single scanning line, with different amplitudes and/or phases (a plurality of rates). Through the above processing, the ultrasound reception circuitry 120 generates a plurality of reflection wave data at each scanning line. Then, the processing circuitry 180 performs an addition/subtraction process to the plurality of reflection wave data at each scanning line, in accordance with a selected modulation method, thereby extracting a harmonic component. Furthermore, the processing circuitry 180 performs envelope detection process or the like to the reflection wave data of the harmonic component, thereby generating B-mode data.

For example, if the PM method is performed, the ultrasound transmission circuitry 110 transmits ultrasound waves of the same amplitude and the reversed phase polarities, for example, (−1, 1), twice at each scanning line, by a scan sequence set by the processing circuitry 180. The ultrasound reception circuitry 120 generates reflection wave data corresponding to "−1" and reflection wave data corresponding to "1". The processing circuitry 180 adds the two reflection wave data. Accordingly, the fundamental wave component is removed, and a signal that mainly contains a second harmonic component is generated. The processing circuitry 180 performs an envelope detection process to the signal, thereby generating B-mode data for the CHI (B-mode data for generating contrast image data).

The B-mode data for the CHI is data expressing a signal intensity of the reflection wave, whose reflection source is the contrast agent, by brightness. When the PM method is performed in the CHI, the processing circuitry 180 can generate the B-mode data to generate living tissue image data by filtering the reflection wave data corresponding to "1".

The Doppler processing function 182 is a function of generating, by analyzing the frequencies of the reception signals received from the ultrasound reception circuitry 120, data (Doppler information) obtained by extracting motion information of a moving object in the region of interest (ROI) that is set in a scan area, based on the Doppler effect. The generated Doppler information is stored in a raw data memory (not shown in the drawings) as Doppler raw data on a two-dimensional ultrasound scan line.

The image generation function 183 is a function of generating B-mode image data based on the data generated by the B-mode processing function 181. The processing circuitry 180, in the image generation function 183, converts (scan-converts) a scan line signal sequence of ultrasound scanning into, for example, a scan line signal sequence in a video format representatively used by television, etc. to generate image data for display. Specifically, the processing circuitry 180 executes RAW-pixel conversion relative to B-mode RAW data stored in a RAW data memory, for example, executes coordinate conversion corresponding to the ultrasound scan state by the ultrasound probe 101, to generate two-dimensional B-mode image data (also referred to as ultrasound image data) consisting of pixels. In other words, by the image generation function 183, the processing circuitry 180 generates a plurality of ultrasound images (medical images) respectively corresponding to a plurality of consecutive frames by transmission and reception of ultrasound waves.

The processing circuitry 180 also converts image data into a video signal by performing various processes, such as dynamic range, brightness, contrast and γ curve corrections, and an RGB conversion, on two-dimensional B-mode image data. The processing circuitry 180 displays a video signal on the display 103. The processing circuitry 180 may generate a graphic user interface (GUI) through which the operator inputs various types of instructions via the input device, and may direct the display 103 to display the GUI.

The system control function 188 is a function of integrally controlling the overall operations of the ultrasound diagnosis apparatus 1. The data generation function 184, the calculation function 185, the display image generation function 186, and the display control function 187 will be described later.

A basic configuration of the ultrasound diagnosis apparatus 1 according to the first embodiment has been described. With the configurations, the ultrasound diagnosis apparatus 1 according to the first embodiment can depict a flow of the contrast agent through the processing described below. For example, the ultrasound diagnosis apparatus 1 can quantitatively display the direction and travel speed of a flow of the contrast agent by tracking each of microbubbles of the contrast agent used in the contrast echo method.

In the embodiment described below, it is assumed that a flow of the contrast agent is depicted by substantially real-time processing for ultrasound image data captured using the contrast agent injected into the subject P. At this time, the image memory 140 stores, for example, a plurality of ultrasound images (medical images) respectively corresponding to a plurality of consecutive frames. However, the embodiment is not limited to this example, and similar processing may be carried out later for ultrasound image data (or reflection wave data or the like) that have already been captured. In the following description, the contrast agent is simply referred to as "bubbles".

The data generation function 184 is a function of specifying a position of the contrast agent in each of two medical images corresponding to adjacent frames. For example, in the data generation function 184, the processing circuitry 180 corrects a motion of a living tissue in each of the two medical images, and specifies a position of the contrast agent in each of the two corrected medical images. The data generation function 184 removes a harmonic component based on the fixed position in each of the two medical images, and specifies the position of the contrast agent using the harmonic component based on the contrast agent in each of the two medical images after the removal.

First, by the data generation function 184, the processing circuitry 180 executes processing of correcting the motion of the living tissue in the contrast image data taken in substantially real time. The motion of the living tissue to be corrected is, for example, a motion of a parenchymal tissue (body motion) of the subject P, or a general position shift of the image due to a displacement (shake) of the ultrasound probe 101. If such a position shift occurs, the position of a bubble depicted in accordance with contrast image data will include the motion of the subject or the displacement of the ultrasound probe 101. In this case, therefore, the motion of the living tissue in the image data is corrected.

For example, the processing circuitry 180 reads living tissue image data of the current frame (also represented as "Nth frame") and living tissue image data of (N−1)th frame from the image memory 140. The living tissue image data is ultrasound image data (B-mode image data) generated on the basis of the fundamental wave component separated by the filtering process from the reflection wave data. The processing circuitry 180 performs pattern matching based on the mutual correlation method between the living tissue image data of the Nth frame and the living tissue image data of the (N−1)th frame, and obtains an amount of shift between the living tissue image data of the Nth frame and the living tissue image data of the (N−1)th frame. Using the obtained amount of shift, the processing circuitry 180 calculates an amount of correction to match the coordinate system of the living tissue image data of the Nth frame with the coordinate system of the living tissue image data of the (N−1)th frame. Using the calculated amount of correction, the processing circuitry 180 corrects the coordinate system of contrast image data of the Nth frame.

Thus, the processing circuitry 180 performs correction of removing the motion of the living tissue (position shift) between the (N−1)th frame and the Nth frame from the contrast image data of the Nth frame. As a result, the processing circuitry 180 corrects the motion of the living tissue in the contrast image data in each of the frames sequentially imaged substantially in real time with reference to the position of the living tissue in the (N−1)th frame.

In the above description, the processing is performed using the living tissue image data based on the fundamental wave component obtained by the filtering process. However, the embodiment is not limited to this description. For example, if contrast image data is generated by the PM method, living tissue image data generated from reflection wave data obtained by the PM method may be used. For example, if reflection wave data is obtained through transmission of ultrasonic waves of (−1, 1) twice by the PM method, B-mode image data obtained from the reflection wave data corresponding to "1" may be used as the living tissue image data described above. Alternatively, B-mode image data obtained from a subtraction signal calculated by subtracting the reflection wave data corresponding to "−1" from the reflection wave data corresponding to "1" may be used as the living tissue image data.

Next, the processing circuitry 180 removes a harmonic component based on a fixed position. The harmonic component based on a fixed position refers to, for example, a harmonic component derived from a living tissue (fixed living tissue) of the subject P or a harmonic component derived from a bubble stagnating in the living body (stagnating bubble). For example, it is known that bubbles are taken into and stagnate within the Kupffer cells of liver tissues. Therefore, the processing circuitry 180 removes the harmonic component based on the fixed position from the contrast image data.

For example, the processing circuitry 180 removes the harmonic component based on the fixed position from the contrast image data after correcting the motion of the living tissue, through statistical processing of signals in the frame direction. As an example, the processing circuitry 180 calculates a dispersion of the values of the respective pixels (signal values) in Nth to (N−10)th contrast image data. If the calculated dispersion value is high, it means that the signal value in the pixel changes with time. Accordingly, it is determined that the harmonic component of the pixel is based on a moving object (i.e., a bubble). On the other hand, if the calculated dispersion value is low, it means that the signal value in the pixel does not change with time. Accordingly, it is determined that the harmonic component of the pixel is based on the fixed position. Therefore, the processing circuitry 180 compares the calculated dispersion value with a threshold value, and removes the harmonic component of the pixel, from which a dispersion value lower than the threshold value is calculated as the harmonic component based on the fixed position.

In this manner, the processing circuitry 180 removes the harmonic component based on the fixed position from the contrast image data after correcting the motion of the living tissue. In the above description, the dispersion value is calculated using the signal values of the Nth frame to the (N−10)th frame. However, the embodiment is not limited to this description. For example, the processing circuitry 180 may calculate a dispersion value using signal values of any number of frames. The processing circuitry 180 may calculate a dispersion value using signal values of any two frames. For example, the processing circuitry 180 may calculate a dispersion value using signal values of two frames of the Nth frame and the (N−10)th frame. In the case of calculating a dispersion value using two frames, it is preferable to use data of two frames separate by several frames, not two consecutive frames.

In the above description, dispersion values of signal values in a plurality of frames are calculated and compared as the statistical processing of signals in the frame direction. However, the embodiment is not limited to this description. For example, the processing circuitry 180 may calculate a statistical value representing variance, such as a standard deviation or a standard error, instead of the dispersion value, and use it in comparison with the threshold value.

The processing circuitry 180 specifies the position of a bubble. For example, the processing circuitry 180 generates contrast image data from which the harmonic component based on the fixed position has been removed, thereby specifying the position of a bubble.

FIG. 2 is a diagram for explaining processing of a data generation function according to the first embodiment. FIG. 2 exemplifies contrast image data, in which the motion of the living tissue has been corrected and from which the harmonic component based on the fixed position has been removed. In FIG. 2, black circles represent the positions of bubbles.

As shown in FIG. 2, by the data generation function 184, each time contrast image data is imaged, the processing circuitry 180 generates contrast image data, in which the motion of the living tissue has been corrected and the harmonic component based on the fixed position has been removed. For example, when contrast image data of the Nth frame as shown in FIG. 2 is generated, the processing circuitry 180 corrects the motion of the living tissue and removes the harmonic component based on the fixed position from the contrast image data of the Nth frame, The processing circuitry 180 specifies, as a bubble position, position (coordinates) of a pixel having a brightness equal to or higher than the threshold value in the generated contrast image data. In the example shown in FIG. 2, the processing circuitry 180 specifies the positions of the black circles as bubble positions. In the contrast image data, the pixel value or signal intensity obtained by a filtering process to emphasize the bubble positions may be subjected to threshold determination. The contrast image data, in which the bubble positions have been specified by the above process, may be referred to as "contrast position data".

In this manner, the processing circuitry 180 specifies the bubble positions. Although the contrast image data generated by the processing circuitry 180 has been explained above as an example, the contrast image data is not limited to be displayed in the display 103. In other words, the process of the processing circuitry 180 may be executed as an internal process of the processing circuitry 180 without displaying the contrast image data in the display 103. This also applies to the descriptions below.

Furthermore, the processing circuitry 180 sets a search range to a medical image corresponding to the Nth frame with reference to a position of the contrast agent in a medical image corresponding to the (N−1)th frame by the data generation function 184. For example, the processing circuitry 180 sets a search range to a current frame based on the bubble position of the preceding frame.

Figure 3:
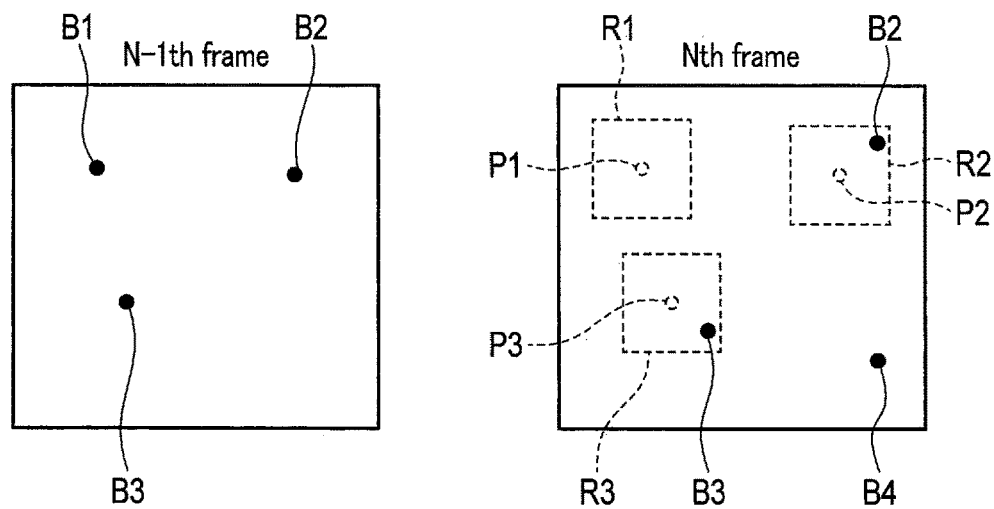
FIG. 3 is a diagram for explaining processing of a data generation function according to the first embodiment.

FIG. 3 is a diagram for explaining processing of a data generation function according to the first embodiment. In each of the contrast image data of the (N−1)th frame and that of the Nth frame, three bubbles are depicted. Bubble IDs "1", "2", and "3" are respectively assigned to bubbles B1, B2, and B3 in the contrast image data of the (N−1)th frame. The bubble IDs are identification numbers to identify the bubbles.

As shown in FIG. 3, the processing circuitry 180 specifies positions of the respective bubbles in the (N−1)th frame in the contrast image data in the Nth frame. Then, the processing circuitry 180 sets, as a search range, a range having a predetermined size and shape around each of the specified positions as the center.

Specifically, the processing circuitry 180 obtains coordinates of the bubble B1 in the (N−1)th frame. Then, the processing circuitry 180 specifies, as a position P1, a position corresponding to the obtained coordinates of the bubble B1 in the contrast image data of the Nth frame. The processing circuitry 180 sets, as a search range R1, a rectangular range of a predetermined size set around the position P1 at the center. The processing circuitry 180 obtains coordinates of the bubble B2 in the (N−1)th frame. Then, the processing circuitry 180 specifies, as a position P2, a position corresponding to the obtained coordinates of the bubble B2 in the contrast image data of the Nth frame. The processing circuitry 180 sets, as a search range R2, a rectangular range of a predetermined size set around the position P2 as the center. The processing circuitry 180 obtains coordinates of the bubble B3 in the (N−1)th frame. Then, the processing circuitry 180 specifies, as a position P3, a position corresponding to the obtained coordinates of the bubble B3 in the contrast image data of the Nth frame. The processing circuitry 180 sets, as a search range R3, a rectangular range of a predetermined size set around the position P3 as the center.

In this manner, the processing circuitry 180 sets search ranges in the contrast image data of the Nth frame based on the bubble positions in the (N−1)th frame. It should be noted that the above explanation is given merely as an example, and the present invention is not limited thereto. For example, the center position of the search range may not necessarily coincide with the bubble position in the (N−1)th frame. Furthermore, for example, the size and shape of the search range may be set discretionarily. Although setting the search range in the contrast image data has been explained above as an example, the contrast image data is not limited to be displayed in the display 103. In other words, the process of the data generation function 184 may be executed as an internal process of the processing circuitry 180 without displaying the contrast image data in the display 103. This also applies to the descriptions below.

The calculation function 185 is a function of calculating a vector representing a movement of the contrast agent. For example, the processing circuitry 180 calculates a vector representing a movement of the contrast agent by the calculation function 185 based on positions of the contrast agent in two medical images corresponding to the adjacent frames. The processing circuitry 180 calculates the vector based on the position of the contrast agent in the search range and the position of the contrast agent which was referred to in order to set the search range.

First, the processing circuitry 180 performs a bubble tracking process. The tracking process is to identify whether each of the bubbles moves, disappears, or newly appears by estimating the relationship between a bubble position in the (N−1)th frame and a bubble position in the Nth frame.

Figure 4:
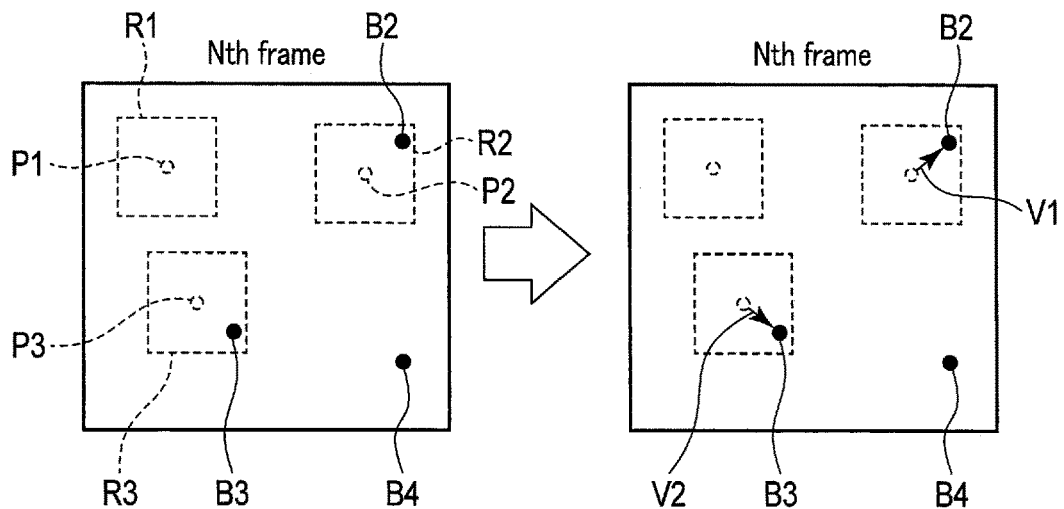
FIG. 4 is a diagram for explaining processing of a calculation function according to the first embodiment.

FIG. 4 is a diagram for explaining processing of calculation function according to the first embodiment. The left part of FIG. 4 shows contrast image data of the Nth frame in which the search ranges R1 to R3 are set.

As shown in the left part of FIG. 4, there is no bubble in the search range R1. The search range R1 is a range set around the position P1 corresponding to the position of the bubble B1 of the (N−1)th frame as the center. In this case, the processing circuitry 180 identifies that the Nth frame does not contain a bubble corresponding to the bubble B1 in the (N−1)th frame. In other words, the processing circuitry 180 identifies that the bubble B1 in the (N−1)th frame has disappeared in the Nth frame. Accordingly, the processing circuitry 180 causes the bubble B1 in the (N−1)th frame to disappear.

The search range R2 contains one bubble. The search range R2 is a range set around the position P2 corresponding to the position of the bubble B2 of the (N−1)th frame as the center. In this case, the processing circuitry 180 identifies that the bubble in the search range R2 corresponds to the bubble B2 in the (N−1)th frame. In other words, the processing circuitry 180 identifies that the bubble in the search range R2 corresponds to the bubble moved from the position P2. Accordingly, the processing circuitry 180 assigns the bubble B2 in the (N−1)th frame to the bubble in the search range R2 (see the right part of FIG. 4).

The search range R3 contains one bubble. The search range R3 is a range set around the position P3 corresponding to the position of the bubble B3 of the (N−1)th frame as the center. In this case, the processing circuitry 180 identifies that the bubble in the search range R3 corresponds to the bubble B3 in the (N−1)th frame. In other words, the processing circuitry 180 identifies that the bubble in the search range R3 corresponds to the bubble moved from the position P3. Accordingly, the processing circuitry 180 assigns the bubble B3 in the (N−1)th frame to the bubble in the search range R3 (see the right part of FIG. 4).

If there is a bubble that is not included in any of the search ranges R1 to R3, the processing circuitry 180 identifies that the bubble newly appears in the Nth frame. In the example of FIG. 4, a bubble B4 in a lower right portion of the Nth frame is not included in any of the search ranges. In this case, the processing circuitry 180 identifies that the bubble in the lower right portion of the Nth frame newly appears. Accordingly, the processing circuitry 180 issues a new bubble ID "4" and assigns it to the bubble B4 which has newly appeared.

A search range may contain two or more bubbles. In this case, the processing circuitry 180 may identify that the bubble which is closest to the bubble position in the (N−1)th frame referred to in order to set the search range or the bubble having a shape most similar to the bubble in the (N−1)th frame is a bubble moved from the (N−1)th frame (moved bubble). Alternatively, the processing circuitry 180 may identify the bubble having the best score based on the distance and shape as a bubble moved from the (N−1)th frame.

Even in the case where there is only one bubble in the search range, the processing of comparing the shape of the bubble in the (N−1)th frame and that of the bubble in the Nth frame may be carried out. In this case, if the similarity is low (lower than a predetermined threshold), the two bubbles are determined to be different. In this case, the processing circuitry 180 identifies that the bubble in the (N−1)th frame has disappeared and the bubble in the Nth frame has newly appeared.

Next, the processing circuitry 180 calculates a vector representing a movement of the contrast agent based on the position of the contrast agent in the current frame and the position of the contrast agent in the preceding frame. For example, the processing circuitry 180 calculates the vector for a bubble which is continuously assigned the bubble ID over the (N−1)th frame and the Nth frame.

In the example shown in FIG. 4, the bubbles B2 and B3 are continuously assigned the bubble IDs over the (N−1)th frame and the Nth frame. In this case, the processing circuitry 180 calculates a vector V1 from the position P2 as a starting point to the position of the bubble B2 of the Nth frame as an ending point in the right part of FIG. 4. The vector V1 represents a direction of movement of the bubble and a moving speed of the bubble. The moving speed of the bubble is calculated by converting the distance between the starting point and the ending point to a length in a real space (pitch size), and dividing the length by a frame interval. With regard to the bubble B3, similarly, the processing circuitry 180 calculates a vector V2 from the position P3 as a starting point to the position of the bubble B3 of the Nth frame as an ending point. Thus, the processing circuitry 180 calculates the moving speed of the contrast agent from the time difference between the adjacent frames and the length in the real space of the vector.

In this manner, the processing circuitry 180 calculates the vectors representing the movements of the bubbles. The explanation above is merely an example and the embodiment is not limited to the explanation. For example, although the calculation of the vectors on the contrast image data has been explained above as an example, the contrast image data is not limited to be displayed in the display 103. In other words, the process of the processing circuitry 180 may be executed as an internal process of the processing circuitry 180 without displaying the contrast image data in the display 103. This also applies to the descriptions below.

Furthermore, the processing circuitry 180 calculates a time difference between one of adjacent frames and a reference frame. For example, the processing circuitry 180 calculates a period of time from a time point when imaging is started to a time point when each bubble is detected, as an arrival time of the bubble. In this case, the imaging time of each frame corresponds to the arrival time. Each time a bubble is detected in each of the frames, the processing circuitry 180 calculates an arrival time of the bubble.

The case of calculating a period of time from an imaging start time to a detection time of each bubble as an arrival time has been explained above; however, the embodiment is not limited to the explanation. For example, the processing circuitry 180 may designate a predetermined time as a reference frame and calculate an elapsed time between the designated reference image and a current image. For example, the processing circuitry 180 may determine, as a reference frame, a frame at a time when a bubble is first detected on the contrast image data after the contrast agent is injected, and calculate an elapsed time from the reference frame as an arrival time of each bubble.

The display image generation function 186 is a function of generating display image data having a shape representing a vector which indicates a movement of a bubble. Specifically, by the display image generation function 186, the processing circuitry 180 assigns a color corresponding to a moving speed calculated by using the vector to a bubble specified in the current frame (a bubble that has been tracked). It is assumed that the processing circuitry 180 maintains the bubble that has been once tracked until the processing ends. Thus, bubbles that have been tracked in each frame are accumulated from the imaging start time to a reference time and indicated in the display image data.

It is assumed that the processing circuitry 180 causes the display 103 not to display a bubble outside the range of a display condition (to be described later) in the display image data. However, the processing circuitry 180 may cause the contrast image data to retain information of the bubble outside the range of the display condition.

FIG. 5 is a diagram for explaining a display example of a color bar according to the first embodiment. The processing circuitry 180 assigns a color corresponding to a predetermined display condition to a bubble that has been tracked. A display condition DC1 shown in FIG. 5 indicates a color bar CB1 having a range from 0 [mm/s] to 100.0 [mm/s]. Thus, in the example shown in FIG. 5, the moving speed of a bubble to be displayed is set, for example, from 0 [mm/s] to 100.0 [mm/s]. The setting of the range of the moving speed may be changed discretionarily.

FIG. 6 is a diagram for explaining a display example of bubbles in contrast image data according to the first embodiment. For example, a bubble B10, a bubble B20, and a bubble B30 represent bubble positions in the (N−1)th frame, and a bubble B11, a bubble B21, and a bubble B31 represent bubble positions in the Nth frame.

The processing circuitry 180 calculates a vector V11 from the position of the bubble B10 as a starting point and the position of the bubble B11 as an ending point. Similarly, the processing circuitry 180 calculates a vector V21 from the position of the bubble B20 as a starting point and the position of the bubble 321 as an ending point. The processing circuitry 180 calculates a vector V31 from the position of the bubble B30 as a starting point and the position of the bubble B31 as an ending point.

The processing circuitry 180 assigns a color corresponding to the moving speed calculated from the vector V11 to the bubble B11. Similarly, the processing circuitry 180 assigns a color corresponding to the moving speed calculated from the vector V21 to the bubble B21. The processing circuitry 180 assigns a color corresponding to the moving speed calculated from the vector V31 to the bubble B31.

In this manner, the processing circuitry 180 assigns colors corresponding to the moving speeds calculated from the vectors to the bubbles. Therefore, the operator can check the speeds of the bubbles that have been tracked in one frame by referring to the contrast image.

Basic processing for tracking bubbles in the ultrasound diagnosis apparatus 1 according to the first embodiment has been described above. With the processing described above, the ultrasound diagnosis apparatus 1 according to the first embodiment can stably track a bubble moving at a low speed by decimation processing described later. In the following, tracking in normal time will be first described, and then tracking of the embodiment with decimation processing will be described.

FIG. 7 is a diagram for explaining a color bar related to display conditions in normal time according to the first embodiment. Tracking of the present embodiment in normal time is utilized in the case of tracking bubbles flowing through, for example, a blood vessel in the living body P.

A display condition DC2 is used to display, for example, tracking in the normal time. The display condition DC2 indicates, for example, a color bar CB2 having a range from 15.0 [mm/s] to 60.0 [mm/s].

In the tracking in the normal time, for example, the lower limit value of the display condition DC2 is determined to be a specific value (15.0 [mm/s] in the example shown in FIG. 7). The moving speed of a bubble is calculated based on the amount of movement of a vector and a frame rate, as described above. Therefore, if the amount of movement of a bubble between frames is too small, the bubble may be determined to have not moved (be stationary) and a vector may not be calculated.

Figure 8:
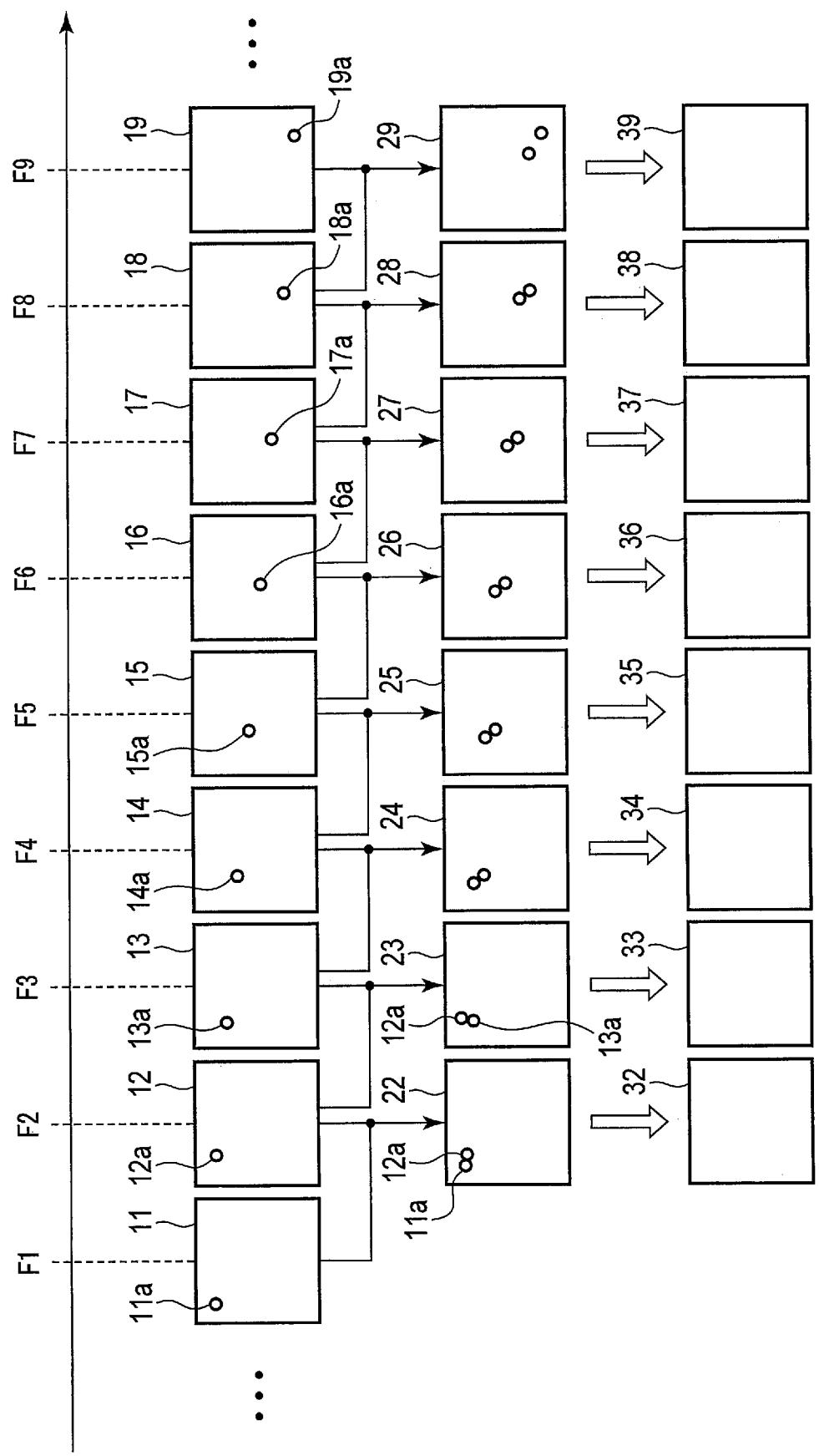
FIG. 8 is a diagram for explaining a generation example of display image data in normal time according to the first embodiment.

FIG. 8 is a diagram for explaining a generation example of display image data in normal time according to the first embodiment. FIG. 8 shows contrast image data 11 to contrast image data 19 respectively corresponding to the frame F1 to the frame F9. In the contrast image data 11 to the contrast image data 19, a bubble 11a to a bubble 19a are respectively specified. It is assumed that the bubble 11a to the bubble 19a are the same bubble. This also applies to the descriptions below.

In the frame F2, as the position of the bubble 11a and the position of the bubble 12a in a calculation region 22 are close, the processing circuitry 180 determines that the bubble 11a and the bubble 12a are stationary bubbles. Since no vector is calculated, the processing circuitry 180 generates display image data 32 which does not include the bubble 12a.

Similarly, in the frame F3, as the position of the bubble 12a and the position of the bubble 13a in a calculation region 23 are close, the processing circuitry 180 determines that the bubble 12a and the bubble 13a are stationary bubbles. Since no vector is calculated, the processing circuitry 180 generates display image data 33 which does not include the bubble 13a.

In the subsequent frames F4 to F9, similarly, since no vector is calculated, the processing circuitry 180 generates display image data 34 to display image data 39 which do not include a bubble.

(Decimation Processing)

Next, tracking utilizing decimation processing according to the present embodiment will be described. The decimation processing is a process of skipping frames when calculating a vector. The term "skipping frames" means that two pieces of contrast image data for use in calculating a vector are spaced by one or more frames. For example, if one frame is skipped, the processing circuitry 180 calculates a vector using contrast image data corresponding to an Nth frame and contrast image data corresponding to an (N−2)th frame. The (N−2)th frame is a frame that is two frames prior to the Nth frame.

By the data generation function 184, the processing circuitry 180 generates first contrast position data and second contrast position data indicating positions of the contrast agent respectively for a first medical image and a second medical image of a plurality of medical images stored in the image memory 140, the first medical image corresponding to a first frame, the second medical image corresponding to a second frame that is two or more frames prior to the first frame.

By the calculation function 185, the processing circuitry 180 calculates a vector representing a movement of the contrast agent based on the generated first contrast position data and second contrast position data.

The display image generation function 186 is a function of generating display image data indicating a flow of the contrast agent. By the display image generation function 186, the processing circuitry 180 generates, for example, display image data having a shape representing the calculated vector.

The display control function 187 is a function of causing the display 103 to display the generated display image data. Specifically, by the display control function 187, the processing circuitry 180 may cause the display 103 to directly display the display image data, or may superimpose the display image data on predetermined medial image data and cause the display 103 to display the superimposed data.

Figure 9:
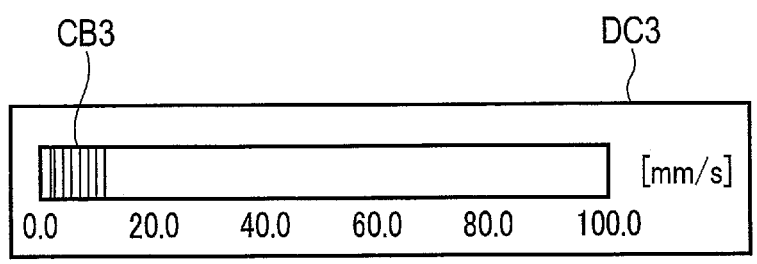
FIG. 9 is a diagram for explaining a color bar related to display conditions in low speed time according to the first embodiment.

FIG. 9 is a diagram for explaining a color bar related to display conditions in low speed time according to the first embodiment. Tracking in low speed time, according to the embodiment, is utilized in tracking a bubble which is liable to stagnate (pool) in a living tissue, such as a tumor.

A display condition DC3 is used to display tracking in, for example, low speed time. The display condition DC3 indicates a color bar CB3 having a range from 1.0 [mm/s] to 15.0 [mm/s]. In the present embodiment, the lower limit value of the display condition DC3 may be lower than the lower limit value of the display condition DC2 mentioned above. This is realized by decimation processing.

Figure 10:
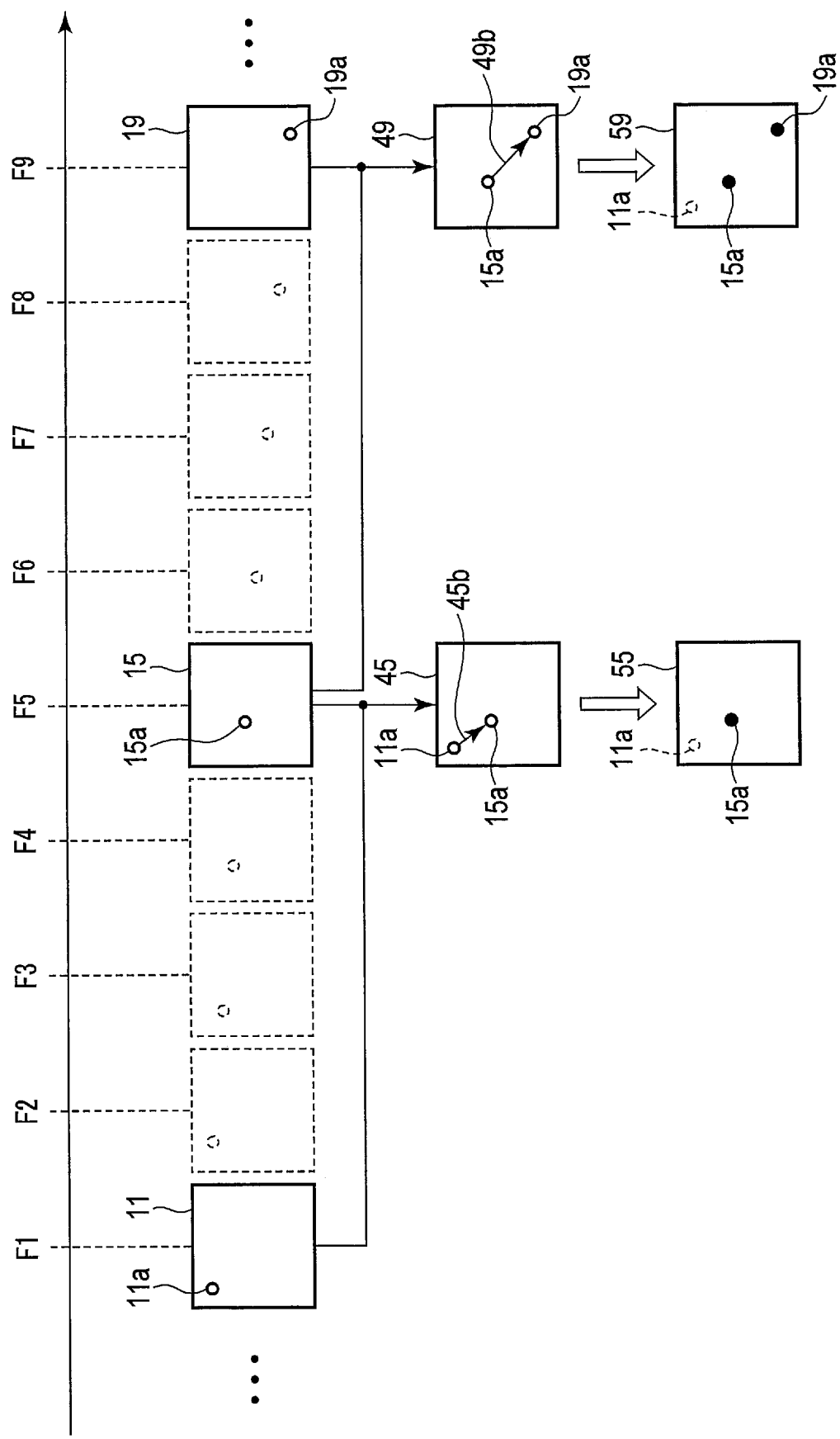
FIG. 10 is a diagram for explaining a generation example of display image data in decimation processing time according to the first embodiment.

FIG. 10 is a diagram for explaining a generation example of display image data in a case of carrying out the decimation process according to the first embodiment. In the example shown in FIG. 10, three frames are skipped to calculate a vector. FIG. 10 shows contrast image data 11, contrast image data 15, and contrast image data 19 respectively corresponding to the frame F1, the frame F5, and the frame F9. In the contrast image data 11, the contrast image data 15, and the contrast image data 19, the bubble 11a, the bubble 15a, and the bubble 19a are respectively specified.

In the frame F5, the processing circuitry 180 determines that the bubble 11a and the bubble 15a in a calculation region 45 are the same bubble. The processing circuitry 180 calculates a vector 45b from the position of the bubble 11a as a starting point and the position of the bubble 15a as an ending point. After calculating the vector 45b, the processing circuitry 180 calculates the moving speed of the bubble 15a based on the vector 45b and the time length of the skipped frames (the time length of the four frames in FIG. 10). After calculating the moving speed of the bubble 15a, the processing circuitry 180 assigns a color corresponding to the moving speed of the bubble 15a to the bubble 15a, and generates display image data 55 including the colored bubble 15a.

Similarly, in the frame F9, the processing circuitry 180 determines that the bubble 15a and the bubble 19a in a calculation region 49 are the same bubble. Then, the processing circuitry 180 calculates a vector 49b from the position of the bubble 15a as a starting point and the position of the bubble 19a as an ending point. After calculating the vector 49b, the processing circuitry 180 calculates the moving speed of the bubble 19a based on the vector 49b and the time length of the skipped frames. After calculating the moving speed of the bubble 19a, the processing circuitry 180 assigns a color corresponding to the moving speed of the bubble 19a to the bubble 19a, and generates display image data 59 including the colored bubble 19a. The display image data 59 includes the colored bubble 15a in the frame F5.

The number of frames to be skipped is not limited to three. For example, the processing circuitry 180 may determine the number of frames to be skipped (the value of a simulative frame rate) in accordance with the upper limit value of the display condition DC3 shown in FIG. 9. The processing circuitry 180 may determine the upper limit value of the display condition DC3 in accordance with the value of a simulative frame rate. The simulative frame rate means that, for example, if the normal frame rate is 60 fps, the frames are thinned by three frames each time (three frames are skipped), so that the total number of frames is thinned to ¼ the original frames and the frame rate thus becomes 15 fps.

Figure 11:
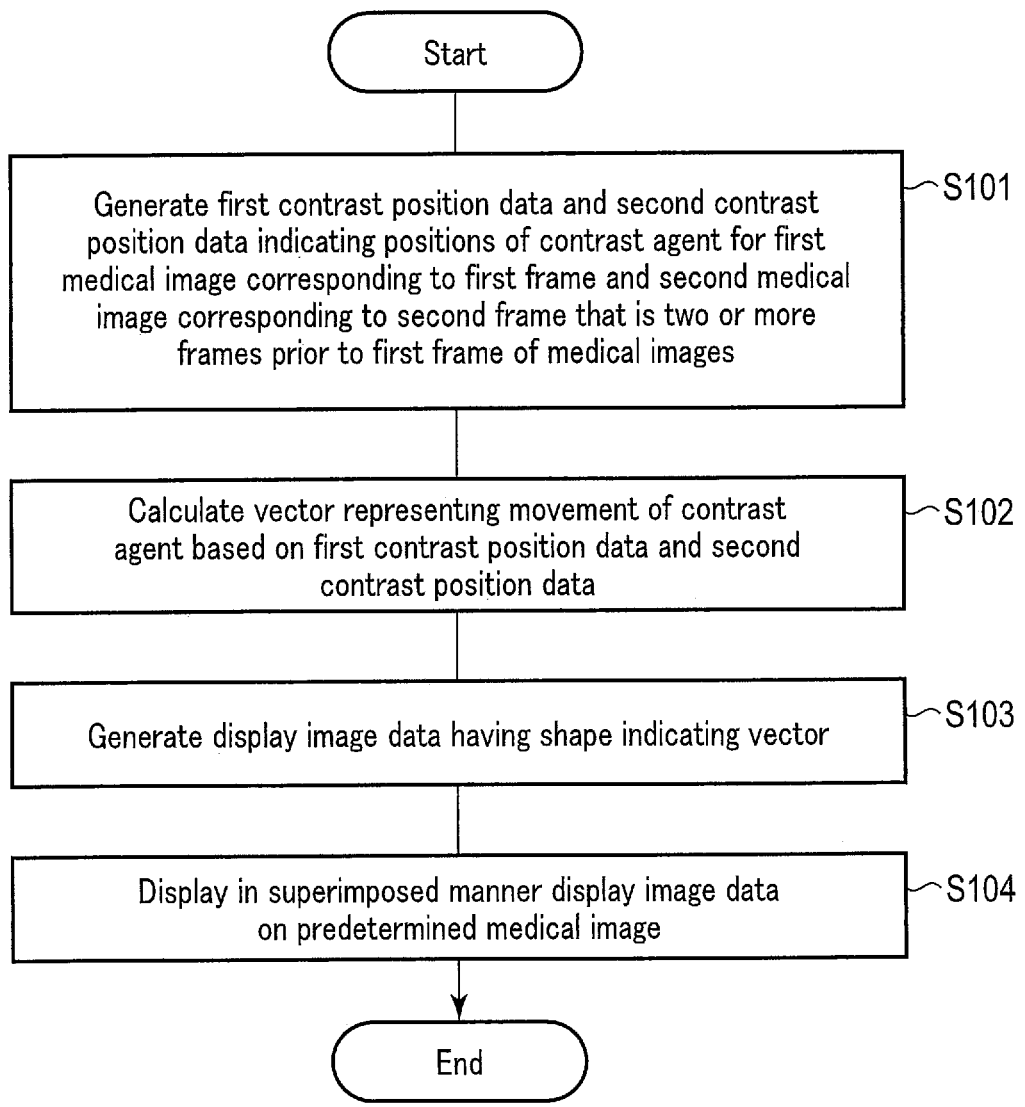
FIG. 11 is a flowchart illustrating an operation of processing circuitry that carries out decimation processing according to the first embodiment.

FIG. 11 is a flowchart illustrating an operation of processing circuitry that carries out decimation processing according to the first embodiment. The process shown in FIG. 11 is started, for example, at reception of an instruction for further performing the decimation processing from the operator during bubble tracking processing by the ultrasound diagnosis apparatus 1. In the following explanation, it is assumed that the processing circuitry 180 has acquired contrast image data of each of the frames which are successively imaged substantially in real time.

(Step S101)

When the decimation processing starts, the processing circuitry 180 performs the data generation function 184. When the data generation function 184 is performed, the processing circuitry 180 generates first contrast position data and second contrast position data indicating positions of the contrast agent respectively for a first medical image and a second medical image of a plurality of medical images (for example, ultrasound images), the first medical image corresponding to a first frame, the second medical image corresponding to a second frame that is two or more frames prior to the first frame.

In the example shown in FIG. 10, the processing circuitry 180 generates data indicating the position of the bubble 15a (first contrast position data) and data indicating the position of the bubble 11a (second contrast position data) for contrast image data 15 (first medical image) corresponding to the frame F5 (first frame) and contrast image data 11 (second medical image) corresponding to the frame F1 (second frame) that is four frames prior to the frame F5.

(Step S102)

After calculating the contrast position data, the processing circuitry 180 performs the calculation function 185. When the calculation function 185 is performed, the processing circuitry 180 calculates a vector representing the position of the contrast agent based on the first contrast position data and the second contrast position data.

In the example shown in FIG. 10, the processing circuitry 180 calculates the vector 45b from the position of the bubble 11a as a starting point and the position of the bubble 15a as an ending point based on the data indicating the position of the bubble 15a (first contrast position data) and the data indicating the position of the bubble 11a (second contrast position data).

(Step S103)

After calculating the vector, the processing circuitry 180 performs the display image generation function 186. When the display image generation function 186 is performed, the processing circuitry 180 generates display image data having a shape indicating the vector.

In the example shown in FIG. 10, the processing circuitry 180 generates the display image data 55 including the colored bubble 15a (the shape indicating the vector)

(Step S104)

After generating the display image data, the processing circuitry 180 performs the display control function 187. When the display control function 187 is performed, the processing circuitry 180 superimposes the display image data on a predetermined medical image and displays the superimposed data. After superimposing the display image data on the predetermined medical image, the processing circuitry 180 repeats step S101 to step S104 until receiving an instruction for ending the decimation processing. As described above in connection with the frame F5 in FIG. 10, if the decimation processing is repeated, the subsequent processing is performed at the frame F9.

Figure 12:
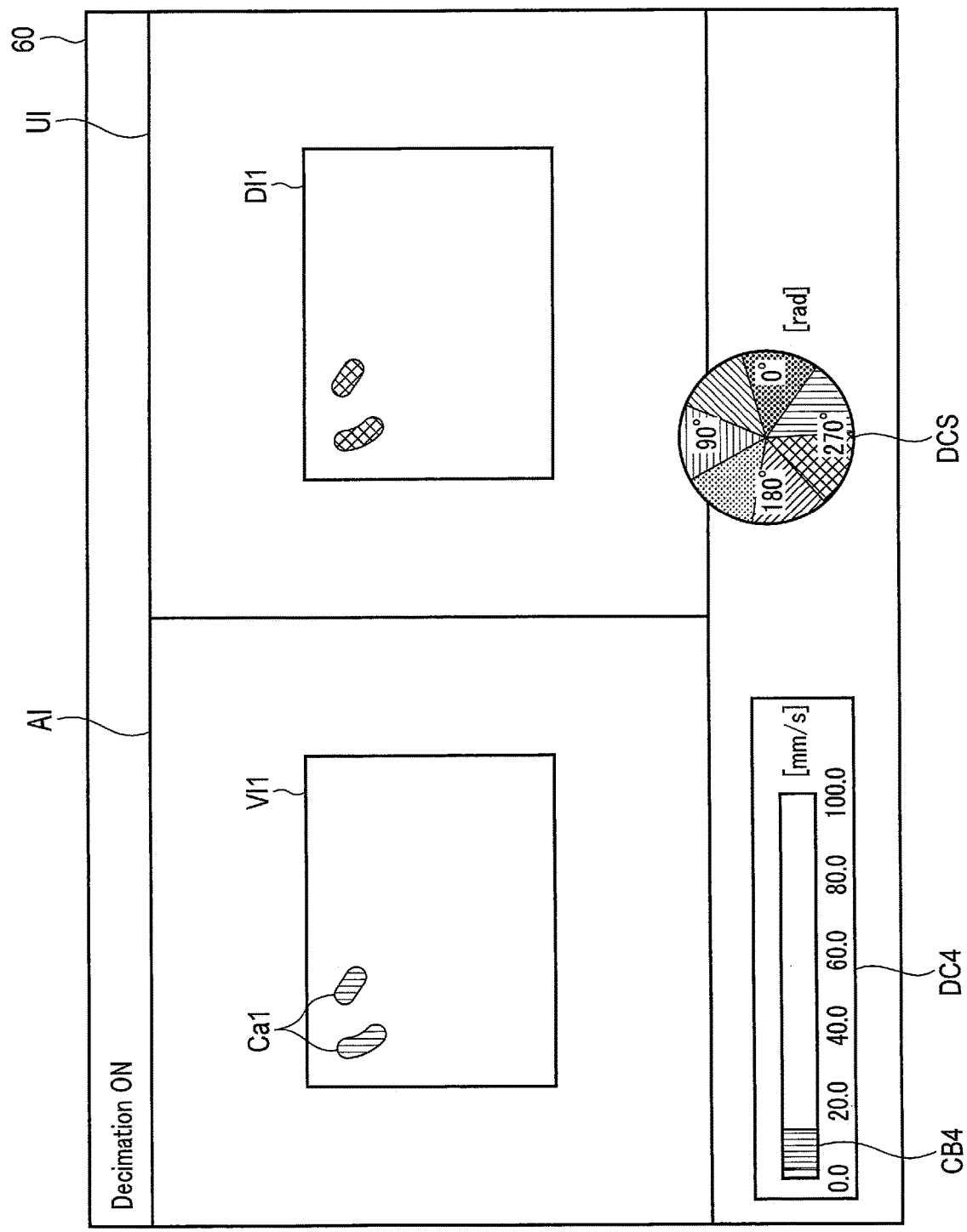
FIG. 12 is a diagram showing a display example of the decimation processing according to the first embodiment.

FIG. 12 is a diagram showing a display example of the decimation processing according to the first embodiment. A display region 60, as shown in FIG. 12, displays a series of letters "Decimation ON" representing that the decimation processing is being performed. An analysis image AI and an ultrasound image UI are displayed side by side in the display region 60.

A region VI1 corresponding to a region of interest is set in the analysis image AI. The data displayed in the region VI1 corresponds to the display image data described above. The region VI1 displays a locus Ca1 representing a continuous movement of a bubble. A color corresponding to a color bar CB4 of a display condition DC4 is assigned to the locus Ca1. In other words, the region VI1 displays a point (or a group of continuous points) to which the color representing the moving speed of a tracked bubble is assigned.

A region DI1 corresponding to the region VI1 is set in the ultrasound image UI. The region DI1 displays a locus corresponding to the direction of a movement of the locus Ca1. A color corresponding to a direction color scale DCS is assigned to the locus in the region DI1. In other words, the region DI1 displays a point (or a group of continuous points) to which the color representing the moving direction of a tracked bubble is assigned.

In the decimation processing described above, the frame rate is simulatively decreased without using the skipped frames, so that a bubble moving at a low speed is tracked. However, the embodiment is not limited to this decimation processing. For example, a pair of frames used to calculate a vector may be shifted, while the number of the frames to be skipped is kept constant.

FIG. 13 is a diagram for explaining another generation example of contrast image data in a case of carrying out the decimation processing according to the first embodiment. FIG. 13 shows contrast image data 11 to contrast image data 19 respectively corresponding to the frame F1 to the frame F9. In the contrast image data 11 to the contrast image data 19, the bubble 11a to the bubble 19a are respectively specified.

The processing in the frame F5 is the same as that as shown in FIG. 10. In the example shown in FIG. 13, processing in the frame F6 is performed after the processing in the frame F5. In the frame F6, the processing circuitry 180 determines that the bubble 12a and the bubble 16a in a calculation region 46 are the same bubble. Then, the processing circuitry 180 calculates a vector 46b from the position of the bubble 12a as a starting point and the position of the bubble 16a as an ending point. After calculating the vector 46b, the processing circuitry 180 calculates the moving speed of the bubble 16a based on the vector 46b and the time length of the skipped frames. After calculating the moving speed of the bubble 16a, the processing circuitry 180 assigns a color corresponding to the moving speed of the bubble 16a to the bubble 16a, and generates display image data 76 including the colored bubble 16a. The display image data 76 includes the colored bubble 15a in the frame F5.

Subsequently, in the same manner, a vector 47b to a vector 49b are assigned respectively to the frame F7 to the frame F9, and colors are assigned to the bubble 17a to the bubble 19a. The display image data 79 in the frame F9 includes the colored bubbles 15a to 19a.

Thus, in the processing exemplified in FIG. 13, the bubbles moving at a low speed can be tracked by skipping frames without decreasing the frame rate.

As described above, the ultrasound diagnosis apparatus according to the first embodiment generates a plurality of ultrasound images (a plurality of medical images) respectively corresponding to a plurality of consecutive frames by transmission and reception of ultrasound waves, generates first contrast position data (first moving-object position data) and second contrast position data (second moving-object position data) indicating positions of the contrast agent (a moving object in a subject) for a first ultrasound image (a first medical image) corresponding to a first frame and a second ultrasound image (a second medical image) corresponding to a second frame that is two or more frames prior to the first frame of a plurality of ultrasound images, calculates a vector representing a movement of the contrast agent (the moving object) based on the first contrast position data and the second contrast position data, and generates display image data having a shape representing the vector.

Thus, since the ultrasound diagnosis apparatus of the embodiment tracks the bubbles (contrast agent) while skipping frames, it can depict a flow of the contrast agent that only moves a little and that is difficult to depict by tracking between adjacent frames (frame by frame).

Second Embodiment

Regarding the first embodiment, the method of tracking bubbles moving at a low speed by the decimation processing has been described. In the second embodiment described below, normal bubble tracking and bubble tracking by the decimation processing are used in combination. In the following description, the processing that uses the two types of tracking in combination is referred to as hybrid processing.

Figure 14:
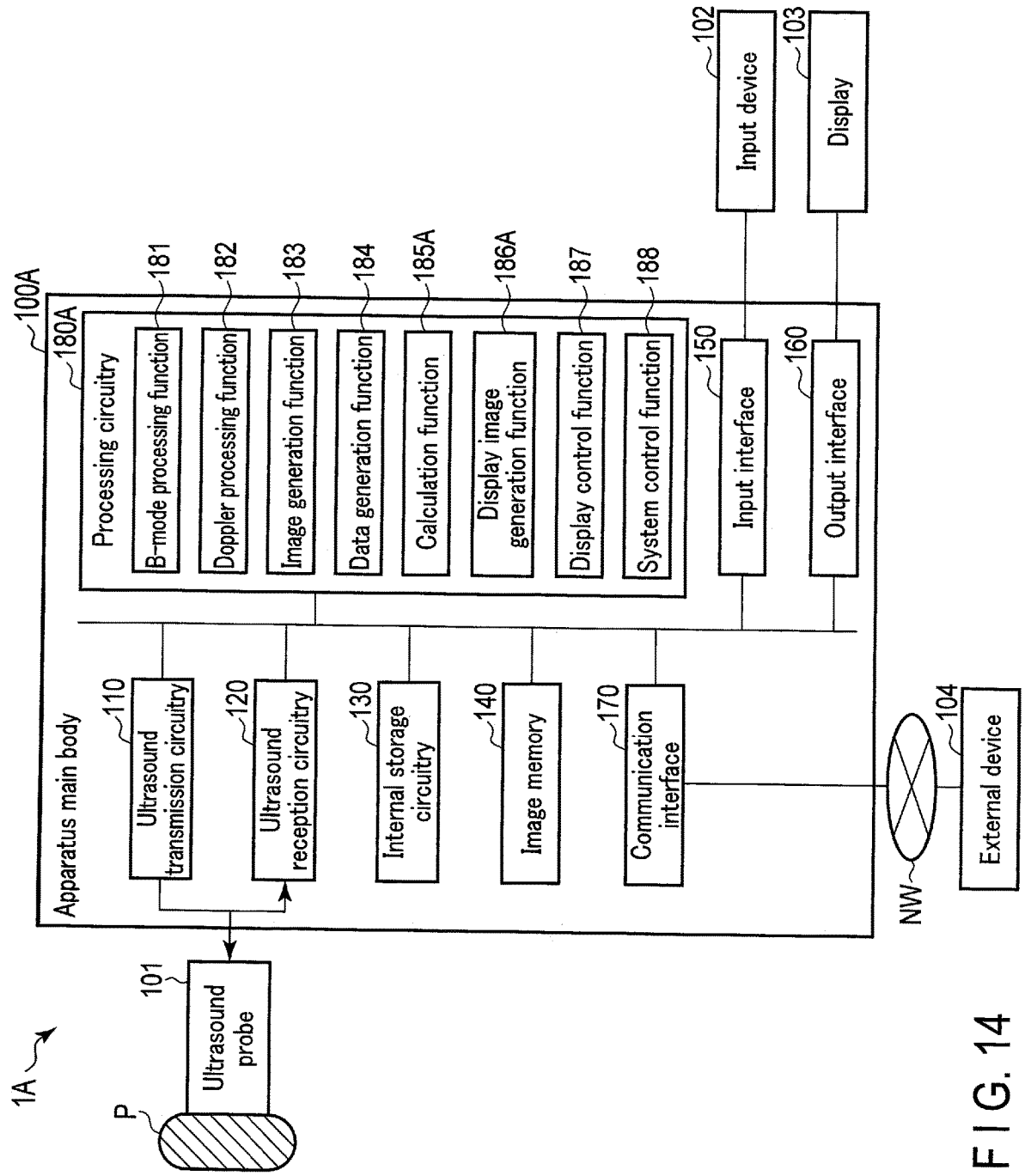
FIG. 14 is a block diagram showing a configuration example of an ultrasound diagnosis apparatus according to a second embodiment.

FIG. 14 is a block diagram showing a configuration example of an ultrasound diagnosis apparatus 1A according to the second embodiment. The ultrasound diagnosis apparatus 1A includes an apparatus main body 100A and an ultrasound probe 101. The apparatus main body 100A is connected to an input device 102 and a display 103. The apparatus main body 100A is connected to an external device 104 via a network NW.

The apparatus main body 100A is an apparatus that generates an ultrasound image based on a reflection wave signal received by the ultrasound probe 101. The apparatus main body 100A includes ultrasound transmission circuitry 110, ultrasound reception circuitry 120, internal storage circuitry 130, an image memory 140, an input interface 150, an output interface 160, a communication interface 170, and processing circuitry 180A.

The processing circuitry 180A is a processor acting as a nerve center of the ultrasound diagnosis apparatus 1A, for example. The processing circuitry 180A implements the program stored in the internal storage circuitry 130, thereby realizing the functions corresponding to the program. The processing circuitry 180A includes, for example, a B-mode processing function 181, a Doppler processing function 182, an image generation function 183 (image generator), a data generation function 184 (data generator), a calculation function 185A (calculator), a display image generation function 186A (display image generator), a display control function 187 (display controller), and a system control function 188.

The calculation function 185A is a function of calculating vectors in different pairs of frames substantially at the same time. The different pairs of frames mean, for example, a pair of a frame F1 and a frame F5 and a pair of a frame F4 and a frame F5.

The display image generation function 186A is a function of generating display image data corresponding to vectors respectively calculated from the different pairs of frames. By the display image generation function 186A, for example, the processing circuitry 180A can generate both of display image data obtained through the normal bubble tracking and display image data obtained through the bubble tracking by the decimation processing.

(Hybrid Processing)

Figure 15:
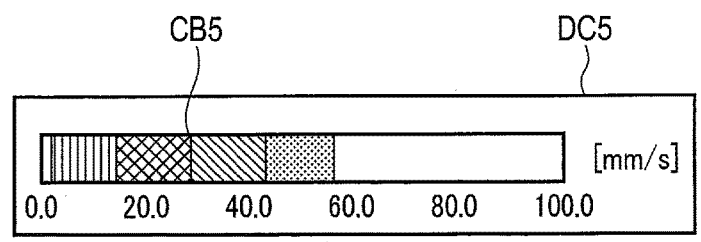
FIG. 15 is a diagram for explaining a color bar used in hybrid processing according to the second embodiment.

FIG. 15 is a diagram for explaining a color bar used in the hybrid processing according to the second embodiment. A display condition DC5 is used to display, for example, tracking in the hybrid processing. The display condition DC5 indicates, for example, a color bar CB5 having a range from 1.0 [mm/s] to 60.0 [mm/s].

Figure 16:
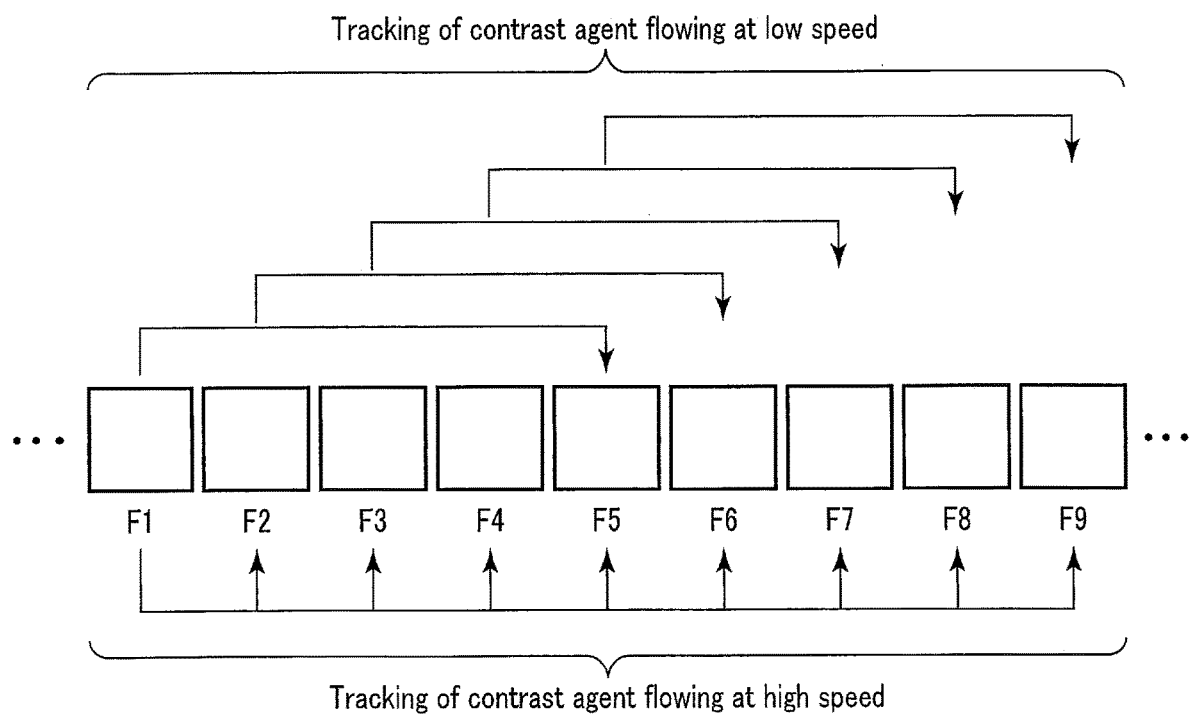
FIG. 16 is a diagram for explaining an outline of the hybrid processing according to the second embodiment.

FIG. 16 is a diagram for explaining an outline of the hybrid processing according to the second embodiment. As described above, the hybrid processing according to the second embodiment uses the normal bubble tracking between adjacent frames and the bubble tracking with skipped frames in combination. The bubble tracking between adjacent frames is used, for example, for tracking a contrast agent (bubble) which flows at a high speed. The bubble tracking with skipped frames is used, for example, for tracking a contrast agent (bubble) which flows at a low speed.

FIG. 17 is a diagram for explaining processing of the display image generation function according to the second embodiment. The processing circuitry 180A generates, by the display image generation function 186A, display image data corresponding to a region VI1 and display image data corresponding to a region VI2. The region VI1 and the region VI2 represent the same region in a contrast image corresponding to a frame.

The region VI1 displays a locus Ca1. A color corresponding to a low-speed area of the color bar CB5 of the display condition DC5 is assigned to the locus Ca1. That is, the display image data corresponding to the region VI1 indicates bubbles which flow at a low speed.

The region VI2 displays a locus Ca2. A color corresponding to a high-speed area of the color bar CB5 of the display condition DC5 is assigned to the locus Ca2. That is, the display image data corresponding to the region VI2 indicates bubbles which flow at a high speed.

After the two pieces of display image data are generated, the processing circuitry 180A causes display image data corresponding to a region VI3 obtained by superimposing the region VI1 and the region VI2 to be displayed by the display control function 187. The display image data displays both the locus Ca1 and the locus Ca2.

Figure 18:
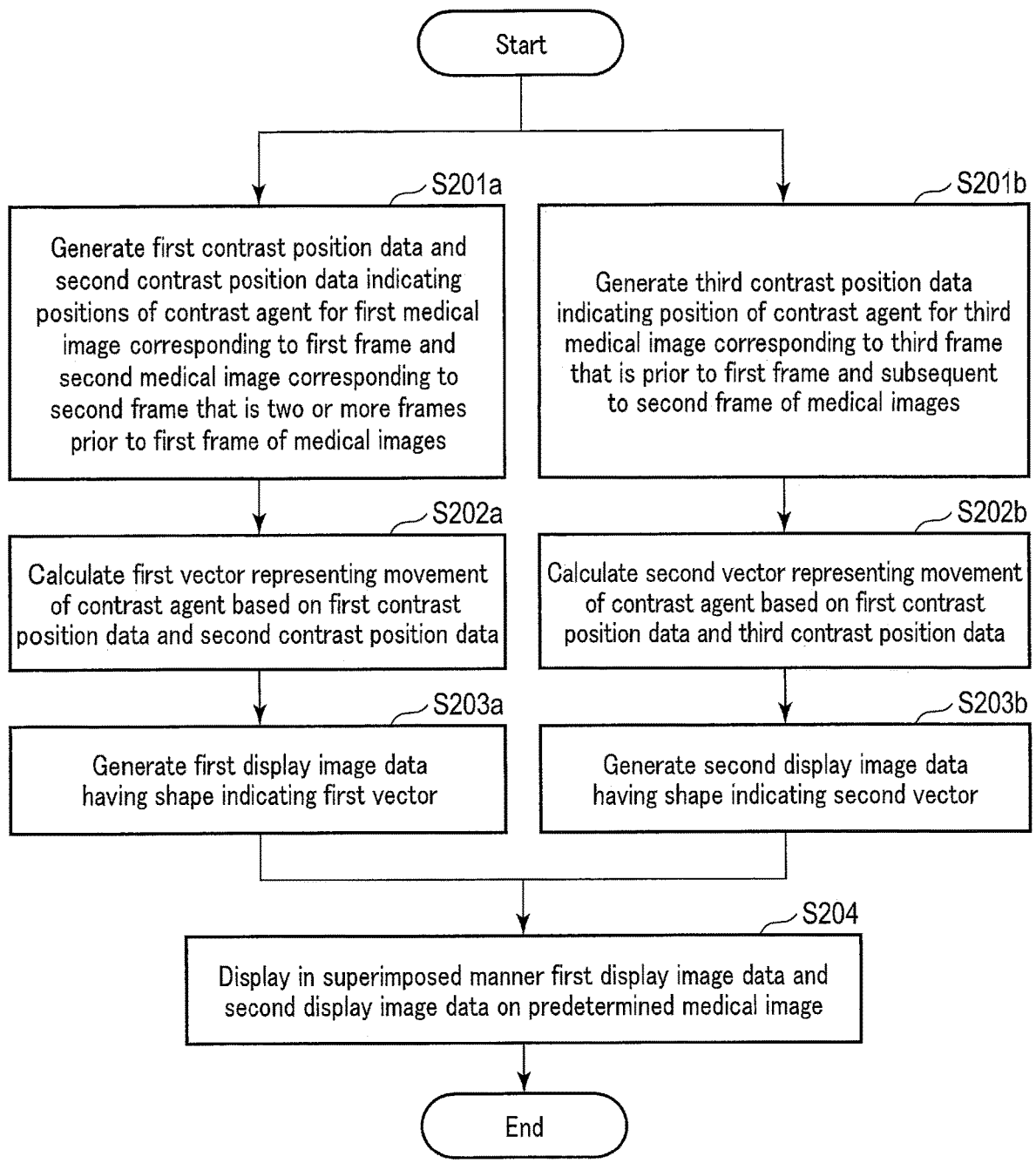
FIG. 18 is a flowchart illustrating an operation of the processing circuitry that carries out the hybrid processing according to the second embodiment.

FIG. 18 is a flowchart illustrating an operation of the processing circuitry that carries out the hybrid processing according to the second embodiment. The process shown in FIG. 18 is started, for example, at reception of an instruction for further performing the hybrid processing from the operator during bubble tracking processing by the ultrasound diagnosis apparatus 1. In the following explanation, it is assumed that the processing circuitry 180A has acquired contrast image data of each of the frames which are successively imaged substantially in real time. A series of step S201a to step S203a corresponds to the bubble tracking by the decimation processing. A series of step S201b to step S203b corresponds to the normal bubble tracking. Those series of steps are executed in parallel substantially simultaneously.

(Step S201a)

When the hybrid processing starts, the processing circuitry 180A performs the data generation function 184. When the data generation function 184 is performed, the processing circuitry 180A generates first contrast position data and second contrast position data indicating positions of the contrast agent respectively for a first medical image and a second medical image of a plurality of medical images (for example, ultrasound images), the first medical image corresponding to a first frame, the second medical image corresponding to a second frame that is two or more frames prior to the first frame.

(Step S202a)

After calculating the contrast position data, the processing circuitry 180A performs the calculation function 185A. When the calculation function 185A is performed, the processing circuitry 180A calculates a first vector representing the position of the contrast agent based on the first contrast position data and the second contrast position data.

(Step S203a)

After calculating the vector, the processing circuitry 180A performs the display image generation function 186A. When the display image generation function 186A is performed, the processing circuitry 180A generates first display image data having a shape indicating the first vector. After step S203a, the processing proceeds to step S204.

(Step S201b)

The processing circuitry 180A performs the processing in step S201b substantially simultaneously with the processing in step S201a. When the data generation function 184 is performed, the processing circuitry 180A generates third contrast position data indicating a position of the contrast agent for a third medical image corresponding to a third frame that is prior to the first frame and subsequent to the second frame of a plurality of medical images (for example, ultrasound images).

(Step S202b)

The processing circuitry 180A performs the processing in step S202b substantially simultaneously with the processing in step S202a. When the calculation function 185A is performed, the processing circuitry 180A calculates a second vector (another vector) representing the position of the contrast agent based on the first contrast position data and the third contrast position data.

(Step S203b)

The processing circuitry 180A performs the processing in step S203b substantially simultaneously with the processing in step S203a. When the display image generation function 186A is performed, the processing circuitry 180A generates second display image data (another display image data) having a shape indicating the second vector. After step S203b, the processing proceeds to step S204.

(Step S204)

After generating the two pieces of display image data, the processing circuitry 180A performs the display control function 187. When the display control function 187 is performed, the processing circuitry 180A superimposes the first display image data and the second display image data on a predetermined medical image and displays the superimposed data. After superimposing the two pieces of display image data on the predetermined medical image, the processing circuitry 180 repeats the series of steps described above until receiving an instruction for ending the hybrid processing.

In step S204, by the display control function 187, the processing circuitry 180A may simultaneously display the first display image data and the second display image data side by side on the predetermined medical image. Thus, the display screen can display in parallel a result of processing of the bubble tracking by the decimation processing and a result of processing of the bubble tracking in normal time.

Figure 19:
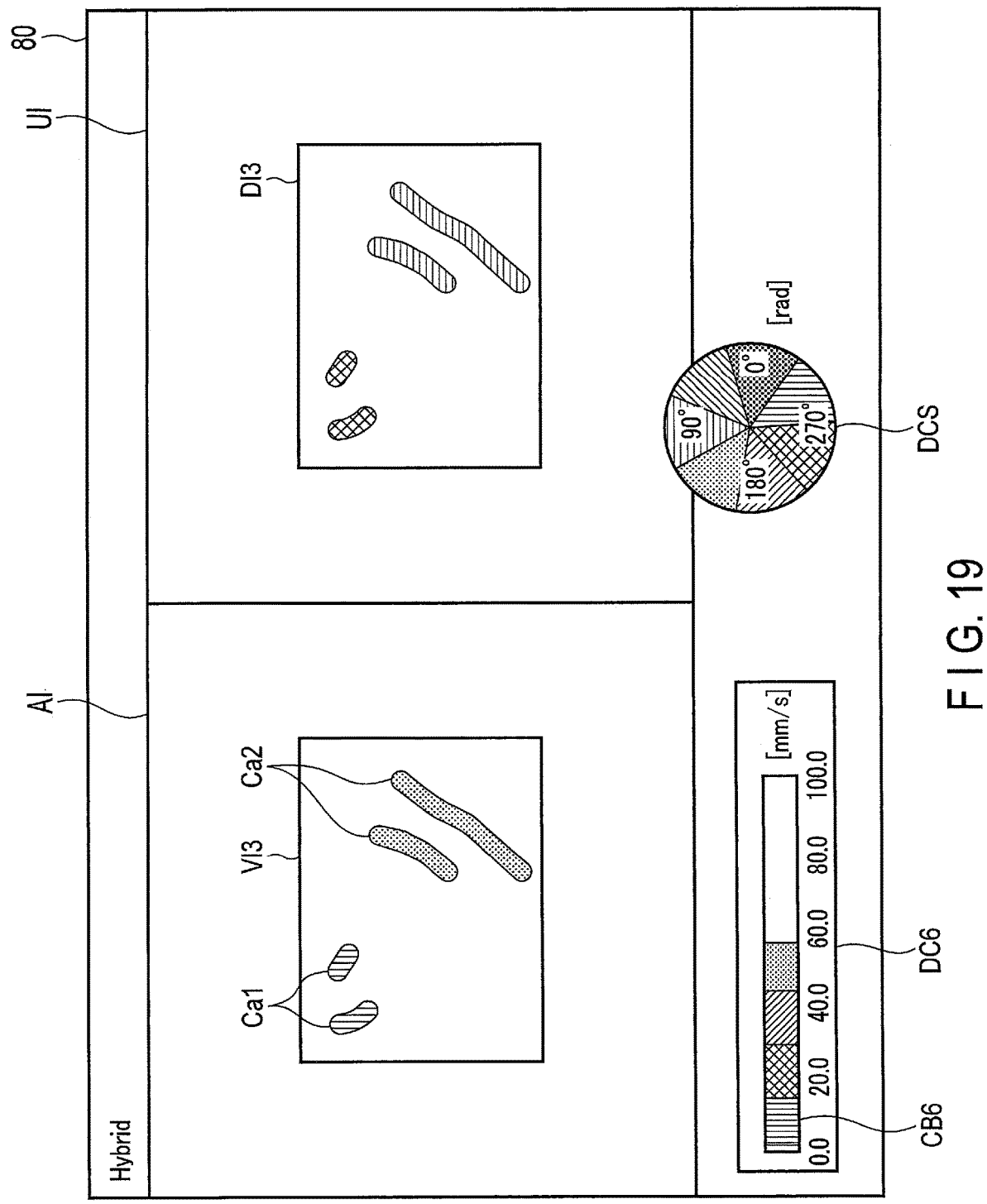
FIG. 19 is a diagram showing a display example of the hybrid processing according to the second embodiment.

FIG. 19 is a diagram showing a display example of the hybrid processing according to the second embodiment. A display region 80, as shown in FIG. 19, displays a series of letters "Hybrid" representing that the hybrid processing is being performed. An analysis image AI and an ultrasound image UI are displayed side by side in the display region 80.

The region VI3 of the analysis image AI displays a locus Ca1 representing movement of bubbles at a low speed and a locus Ca2 representing movement of bubbles at a high speed. Colors corresponding to a color bar CB6 of a display condition DC6 are assigned to the locus Ca1 and the locus Ca2. In other words, the region. VI3 displays a point (or a group of continuous points) to which the colors representing the moving speeds of the bubbles tracked by different means are assigned.

The region DI3 in the ultrasound image UI displays a locus corresponding to the direction of a movement of each of the locus Ca1 and the locus Ca2. Colors corresponding to a direction color scale DCS are assigned to those loci. In other words, the region DI3 displays a point (or a group of continuous points) to which the colors representing the moving directions of the bubbles tracked by different means are assigned.

As described above, the ultrasound diagnosis apparatus according to the second embodiment generates a plurality of ultrasound images (a plurality of medical images) respectively corresponding to a plurality of consecutive frames by transmission and reception of ultrasound waves, generates first contrast position data and second contrast position data indicating positions of the contrast agent for a first medical image corresponding to a first frame and a second medical image corresponding to a second frame that is two or more frames prior to the first frame of a plurality of medical images, calculates a vector (first vector) representing a movement of the contrast agent based on the first contrast position data and the second contrast position data, and generates display image data (first display image data) having a shape representing the vector (first vector). At the same time, the ultrasound diagnosis apparatus of the embodiment generates third contrast position data indicating a position of the contrast agent for a third medical image corresponding to a third frame that is prior to the first frame and subsequent to the second frame of a plurality of medical images, calculates another vector (second vector) representing a movement of the contrast agent based on the first contrast position data and the third contrast position data, and generates display image data (second display image data) having a shape representing the vector (second vector).

Thus, the ultrasound diagnosis apparatus of the embodiment can depict a flow of a contrast agent that moves largely, such as a bubble in a blood vessel, simultaneously with a flow of a contrast agent that moves a little and cannot be easily be depicted by tracking between adjacent frames.

Furthermore, the ultrasound diagnosis apparatus of the embodiment can display at least one of display image data or another display image data. Therefore, the ultrasound diagnosis apparatus of the embodiment can switch between a display in tracking in normal time and a display in tracking at a low speed (decimation processing).

The ultrasound diagnosis apparatus of the embodiment can also display both display image data and another display image data simultaneously side by side. Therefore, the ultrasound diagnosis apparatus of the embodiment can present a result of processing of bubble tracking through decimation processing and a result of processing of bubble tracking in normal time in such a manner that the operator can easily compare the results.

Third Embodiment

Regarding the second embodiment, the method of tracking bubbles moving at a low speed and bubbles moving at a high speed by the hybrid processing has been described. In the description of the third embodiment below, the same bubble is tracked in both of two different types of tracking in the hybrid processing. In the third embodiment, the first contrast position data, the second contrast position data, and the third contrast position data are the same as those in the second embodiment described above.

Figure 20:
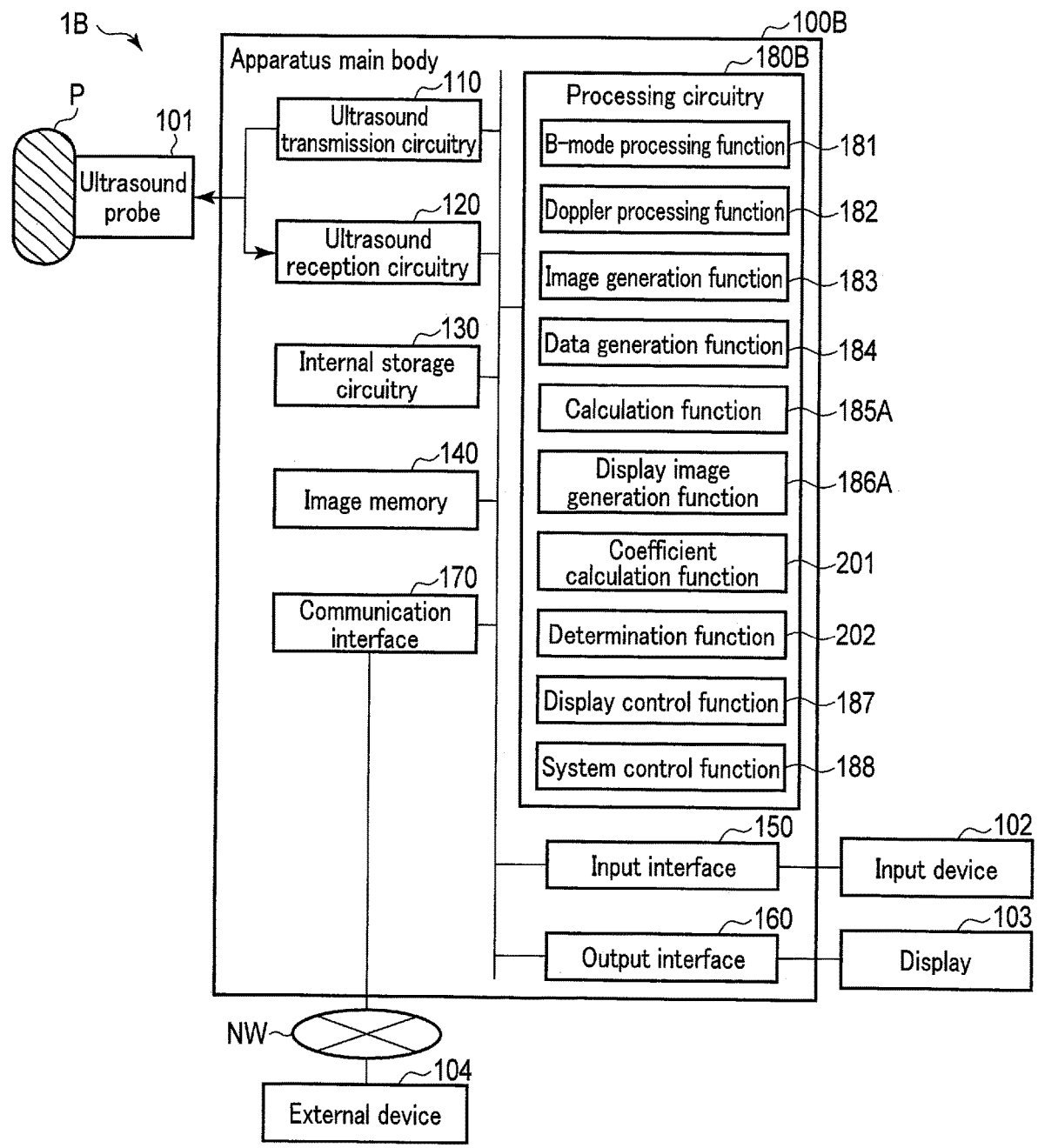
FIG. 20 is a block diagram showing a configuration example of an ultrasound diagnosis apparatus according to a third embodiment.

FIG. 20 is a block diagram showing a configuration example of an ultrasound diagnosis apparatus 1B according to the third embodiment. The ultrasound diagnosis apparatus 1B includes an apparatus main body 100B and an ultrasound probe 101. The apparatus main body 100B is connected to an input device 102 and a display 103. The apparatus main body 100B is connected to an external device 104 via a network NW.

The apparatus main body 100B is an apparatus that generates an ultrasound image based on a reflection wave signal received by the ultrasound probe 101. The apparatus main body 100B includes ultrasound transmission circuitry 110, ultrasound reception circuitry 120, internal storage circuitry 130, an image memory 140, an input interface 150, an output interface 160, a communication interface 170, and processing circuitry 180B.

The processing circuitry 180B is a processor acting as a nerve center of the ultrasound diagnosis apparatus 1B, for example. The processing circuitry 180B implements the program stored in the internal storage circuitry 130, thereby realizing the functions corresponding to the program. The processing circuitry 180B includes, for example, a B-mode processing function 181, a Doppler processing function 182, an image generation function 183 (image generator), a data generation function 184 (data generator), a calculation function 185A (calculator), a display image generation function 186A (display image generator), a coefficient calculation function 201 (coefficient calculator), a determination function 202 (determiner), a display control function 187 (display controller), and a system control function 188.

The coefficient calculation function 201 is a function of calculating a first correlation coefficient of the first contrast position data and the second contrast position data, and a second correlation coefficient of the first contrast position data and the third contrast position data. For example, by the coefficient calculation function 201, the processing circuitry 180 calculates a correlation coefficient using pattern matching (the mutual correlation method) used in the tracking processing.

If frames between the two pieces of contrast position data to calculate a correlation coefficient are skipped, the processing circuitry 180 may utilize an average of correlation coefficients of adjacent frames. Specifically, in the case of calculating a correlation coefficient of two pieces of contrast position data respectively corresponding to the frame F1 and the frame F5, the processing circuitry 180 may utilize an average of the correlation coefficient of two pieces of contrast position data respectively corresponding to the frame F1 and the frame F2, the correlation coefficient of two pieces of contrast position data respectively corresponding to the frame F2 and the frame F3, the correlation coefficient of two pieces of contrast position data respectively corresponding to the frame F3 and the frame F4, and the correlation coefficient of two pieces of contrast position data respectively corresponding to the frame F4 and the frame F5.

The determination function 202 is a function of comparing similarity between the first contrast position data and the second contrast position data with similarity between the first contrast position data and the third contrast position data, and outputting an instruction relating to a display of the display image data or the other display image data corresponding to the higher similarity.

Specifically, if the similarity indicates a correlation coefficient representing a correlation between two pieces of contrast position data, the processing circuitry 180B, by the determination function 202, compares the first correlation coefficient and the second correlation coefficient, and outputs instructions relating to a display of the display image data or the other display image data corresponding to the higher correlation coefficient.

FIG. 21 is a diagram for explaining processing of a determination function and a display image generation function according to the third embodiment. By the display image generation function 186A, the processing circuitry 180B generates display image data corresponding to a region VI4 and display image data corresponding to a region VI5. The region VI4 and the region VI5 are the same region of the contrast image corresponding to a frame.

The region VI4 displays a locus Ca1 and a locus Ca3. A color corresponding to a semi-low-speed area of the color bar CB5 of the display condition DC5 (in FIG. 15, for example, around 20.0 [mm/s]) is assigned to the locus Ca3.

The region VI5 displays a locus Cat and a locus Ca4. A color corresponding to a semi-low-speed area of the color bar CB5 of the display condition DC5 is assigned to the locus Ca4.

In FIG. 21, the locus Ca3 and the locus Ca4 at least partially overlap. With respect to the overlapping loci, the processing circuitry 180B compares, by the determination function 202, the similarity in the region VI4 and the similarity in the region VI5 for each frame, and outputs an instruction relating to the display of the display image data corresponding to the region having the higher similarity. By the display control function 187, the processing circuitry 180B causes the display 103 to display the display image data in accordance with the instruction. In the example shown in FIG. 21, by the determination function 202, the processing circuitry 180B determines that not the locus Ca3 but the locus Ca4 is to be displayed as a determination result.

After performing the determination about the overlapping loci, by the display control function 187, the processing circuitry 180B causes display image data corresponding to a region VI6 obtained by overlapping the region VI4 and the region VI5 to be displayed. The display image data displays the locus Ca1, the locus Ca2 and the locus Ca4.

As described above, the ultrasound diagnosis apparatus according to the third embodiment can perform the following processing in addition to the processing performed by the ultrasound diagnosis apparatus of the second embodiment. The ultrasound diagnosis apparatus of the present embodiment compares the similarity between the first contrast position data and the second contrast position data with the similarity between the first contrast position data and the third contrast position data, outputs an instruction relating to a display of the display image data or the other display image data corresponding to the higher similarity, and displays the display image data or the other display image data in accordance with the instruction. Alternatively, the ultrasound diagnosis apparatus of the present embodiment calculates a first correlation coefficient of the first contrast position data and the second contrast position data and a second correlation coefficient of the first contrast position data and the third contrast position data, compares the first correlation coefficient with the second correlation coefficient, outputs an instruction relating to a display of the display image data or the other display image data corresponding to higher correlation coefficient, and displays the display image data or the other display image data in accordance with the instruction.

Fourth Embodiment

Regarding each of the above embodiments, the ultrasound diagnosis apparatus having a plurality of functions relating to the decimation processing, the hybrid processing, etc. has been described. Regarding the fourth embodiment, an analysis apparatus having the functions mentioned above will now be described. An analysis apparatus having the functions of the third embodiment will be described below as an example; however, the embodiment is not limited to the following description and some of the functions may be omitted.

Figure 22:
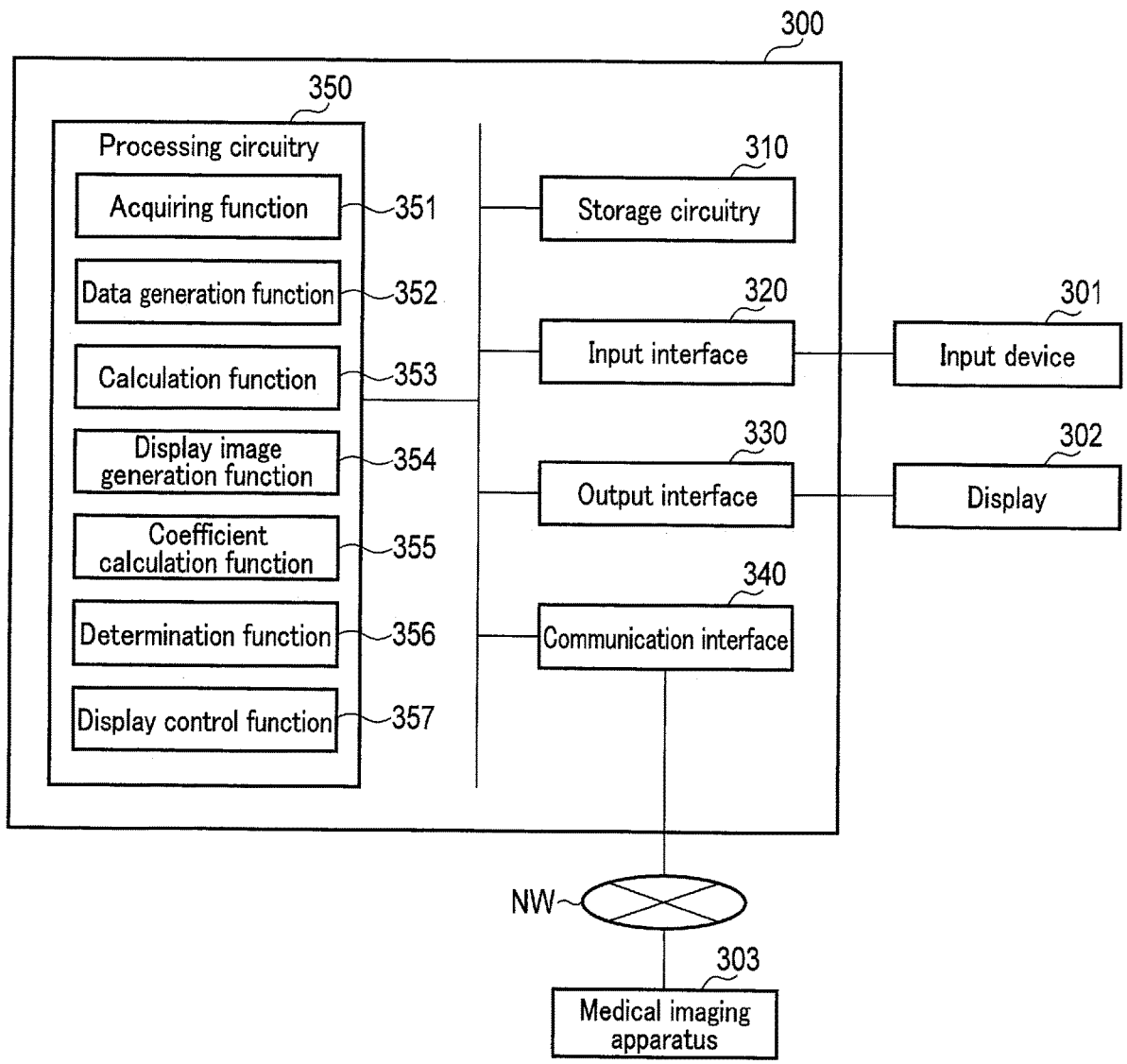
FIG. 22 is a block diagram showing a configuration example of an analysis apparatus according to a fourth embodiment.

FIG. 22 is a block diagram showing a configuration example of an analysis apparatus 300 according to the fourth embodiment. The analysis apparatus 300 is connected to an input device 301 and a display 302. The analysis apparatus 300 is connected to a medical imaging apparatus 303 via a network NW. The input device 301 and the display 302 are substantially the same as the input device 102 and the display 103. A medical imaging apparatus 303 corresponds to, for example, an ultrasound diagnosis apparatus The analysis apparatus 300 performs the decimation processing and the hybrid processing, and generates display image data. The analysis apparatus 300 includes storage circuitry 310, an input interface 320, an output interface 330, a communication interface 340, and processing circuitry 350.

The storage circuitry 310 includes, for example, a magnetic or optical storage medium, or a processor-readable storage medium such as a semiconductor memory. The storage circuitry 310 stores therein a program, various data or the like for realizing the decimation processing, the hybrid processing, etc. The program and data may be pre-stored in the storage circuitry 310. Alternatively, the program and data may be stored and distributed in a non-transitory storage medium, read from the non-transitory storage medium and installed in the storage circuitry 310. The storage circuitry 310 stores S mode image data and contrast image data generated at the medical imaging apparatus 303, in accordance with an operation that is input via the input interface 320.

The storage circuitry 310 may be a drive, etc., which reads and writes various types of information to and from a portable storage medium, such as a CD-ROM drive, a DVD drive, and a flash memory. The storage circuitry 310 may write the stored data onto a portable storage medium to store the data into an external device by way of the portable storage medium.

The input interface 320 receives various instructions from the operator through the input device 301. The input interface 320 is coupled to the processing circuitry 350 via a bus, for example, so that it can convert an operation instruction that is input by the operator, to an electric signal, and output the electric signal to the processing circuitry 350. The input interface 320 is not limited to physical operation components such as a mouse and a keyboard. Examples of the input interface may include a circuit configured to receive an electric signal corresponding to an operation instruction that is input from an external input device provided separately from the analysis apparatus 300 and to output this electric signal to the processing circuitry 350.

The output interface 330 is an interface to output, for example, the electric signal from the processing circuitry 350 to the display 302. The output interface 330 is connected to the processing circuitry 350, for example, via a bus, and outputs the electric signal coming from the processing circuitry 350 to the display 302.

The communication interface 340 is connected to the medical imaging apparatus 303 via, for example, the network NW, and performs data communication with the medical imaging apparatus 303.

The processing circuitry 350 is a processor acting as a nerve center of the analysis apparatus 300, for example. The processing circuitry 350 executes the programs stored in the storage circuitry 310, thereby realizing the functions corresponding to the programs. The processing circuitry 350 includes, for example, an acquiring function 351 (acquirer), a data generation function 352 (data generator), a calculation function 353 (calculator), a display image generation function 354 (display image generator), a coefficient calculation function 355, a determination function 356, and a display control function 357 (display controller).

The acquiring function 351 is a function of acquiring a plurality of medical images respectively corresponding to a plurality of consecutive frames from the medical imaging apparatus 303 or the like. By the acquiring function 351, upon receipt of an instruction for performing the decimation processing and the hybrid processing input via the input device 301, the processing circuitry 350 acquires a plurality of medical images. The processing circuitry 350 outputs an instruction relating to a display of the display image data or the other display image data.

The data generation function 352, the calculation function 353, the display image generation function 354, the coefficient calculation function 355, the determination function 356, and the display control function 357 respectively are functions substantially the same as the data generation function 184, the calculation function 185A, the display image generation function 186A, the coefficient calculation function 201, the determination function 202, and the display control function 187 of the third embodiment.

As described above, the analysis apparatus according to the fourth embodiment acquires a plurality of medical images respectively corresponding to a plurality of consecutive frames, generates first contrast position data (first moving-object position data) and second contrast position data (second moving-object position data) indicating positions of the contrast agent (a moving object in a subject) for a first medical image corresponding to a first frame and a second medical image corresponding to a second frame that is two or more frames prior to the first frame of a plurality of medical images, calculates a vector representing a movement of the contrast agent (the moving object) based on the first contrast position data and the second contrast position data, and generates display image data having a shape representing the vector. Furthermore, the analysis apparatus of the present embodiment can execute the decimation processing and the hybrid processing in the first to third embodiments.

Thus, it is expected that the analysis apparatus of the embodiment can produce the same effects as that of each of the first to third embodiments.

Other Embodiments

In the embodiments described above, the number of frames to be skipped in the decimation processing is described as being constant, but the embodiment is not limited to the description. For example, the number of frames to be skipped may be varied. Other embodiments, in which the number of frames to be skipped in the decimation processing is varied, will be described. In the following, the decimation processing of skipping a variable number of frames is referred to as "variable decimation processing" to be distinguished from a decimation processing of skipping a fixed number of frames (fixed decimation processing). The variable decimation processing may be executed by the processing circuitry 180, 180A, 180B, or 350 described above.

In the fixed decimation processing, the number of frames to be skipped is determined based on the minimum moving speed of bubbles as a reference. In other words, in the fixed decimation processing, the limit of detecting a low-speed bubble is determined in accordance with an interval of skipped frames. Thus, in the fixed decimation processing, the number of frames to be skipped is substantially correlated with the minimum moving speed of bubbles.

On the other hand, the variable decimation processing is performed in accordance the amount of movement of bubbles. For example, in the variable decimation processing, bubble tracking is performed in all frames, and a bubble that moves by a predetermined amount or more is determined to be a moving bubble.

As a specific example, referring to FIG. 8, in the variable decimation processing, it is assumed that the frame F1 and each of the subsequent frames F2, F3, . . . are subjected to vector calculation. In the frame F2, since the amount of movement of the bubble is less than the predetermined amount, the bubble 12a is specified to be a stationary bubble. In the frame F3, since the amount of movement of the bubble is equal to or more than the predetermined amount, the bubble 13a is specified to be a moving bubble.

After the bubble in the frame F3 is specified to be a moving bubble, the frame F3 and each of the subsequent frames F4, F5, F6, . . . are subjected to vector calculation in the variable decimation processing. In the frame F4, since the amount of movement of the bubble is less than the predetermined amount, the bubble 14a is specified to be a stationary bubble. In the frame F5, since the amount of movement of the bubble is less than the predetermined amount, the bubble 15a is specified to be a stationary bubble. In the frame F6, since the amount of movement of the bubble is equal to or more than the predetermined amount, the bubble 16a is specified to be a moving bubble.

Subsequently, the variable decimation processing subjects a frame in which a bubble is specified to be moving and a subsequent frame to the vector calculation.

Thus, in the variable decimation processing, the frames are skipped to calculate a vector by specifying a moving bubble. In the example described above, the pairs of frames used to calculate vectors are the frames F1 and F3 and the frames F4 and F6. In this case, one frame and two frames are respectively skipped from those frames.

As described above, in the variable decimation processing, the number of frames to be skipped is determined based on the amount of movement of the bubble. Accordingly, even if a bubble temporarily stagnates, the variable decimation processing can accurately track the bubble.

The variable decimation processing includes the following two cases to which the skipping of the variable number of frames is applied. First, the decimation processing is applied to all bubbles contained in the frame. This is referred to as first variable decimation processing. Second, the interval of skipped frames in the fixed decimation processing is varied at regular time intervals. This is referred to as second variable decimation processing.

The first decimation processing is applied to all bubbles specified in each frame. Therefore, in the first decimation processing, a pair of frames to calculate a vector is determined in units of bubbles to be specified. Specifically, for example, it is assumed that a bubble A and a bubble B are specified in the frame F1. In this case, if the bubble A moves at a high speed, a vector is calculated using a pair of frames F1 and F3, and if the bubble B moves at a low speed, a vector is calculated using a pair of frames F1 and F5.

The second decimation processing is applied after the first decimation processing is performed, for example, during pre-scanning. Specifically, by the first decimation processing, a predominant speed range of all bubbles in a frame is calculated, and a skipping interval is determined based on the predominant speed range and set uniformly for all frames. Then, pre-scanning is performed at regular time intervals, and the interval of skipped frames is fed back to all frames.

As described above, the variable decimation processing can determine the number of frames to be skipped depending on the amount of movement of the bubble. Therefore, the variable decimation processing can vary the number of frames to be skipped when calculating a vector.

Application Example

In the specification of the present application, the contrast agent is described as a target of tracking. However, the target of tracking is not limited to the contrast agent. The target of tracking may be any moving object that is moved in the subject. For example, the moving object may be a red blood cell in a blood vessel. Therefore, the term "contrast position data" in the specification may be reworded to the term "moving-object position data".

According to at least one of the embodiments described above, it is possible to depict a flow of a moving object in the subject that moves a little.

While several embodiments have been described, these embodiments have been presented by way of example and are not intended to limit the scope of the invention. The embodiments described herein may be embodied in a variety of other forms; furthermore, various omissions, substitutions, changes or combinations of the embodiments may be made without departing from the spirit of the inventions. These embodiments and modifications thereof are included in the scope and spirit of the invention, and are similarly included in the inventions claimed in the patent claims and in the scope of equivalents of the inventions.

The invention claimed is:

1. An analysis apparatus for presenting results of a hybrid processing including a first bubble tracking process including decimation processing and a second bubble tracking process using processing different from the decimation processing, the analysis apparatus comprising:
    processing circuitry configured to
        acquire a plurality of medical images respectively corresponding to a plurality of consecutive frames, the medical images being obtained from a medical scan of a subject using a medical scanning apparatus;
        generate first moving-object position data indicating a position of a moving object in the subject from a first medical image of the plurality of medical images, the first medical image corresponding to a first frame, the moving object being a contrast agent bubble or a red blood cell;
        generate second moving-object position data indicating a position of the moving object in the subject from a second medical image of the plurality of medical images, the second medical image corresponding to a second frame that is two or more frames prior to the first frame;
        generate third moving-object position data indicating a position of the moving object from a third medical image of the plurality of medical images, the third medical image corresponding to a third frame that is prior to the first frame and subsequent to the second frame;
        calculate a vector representing a movement of the moving object, using the first bubble tracking process including the decimation processing, based on only the generated first moving-object position data and the generated second moving-object position data;
        calculate another vector representing a movement of the moving object, using the second bubble tracking process different from the first bubble tracking process, based on only the generated first moving-object position data and the generated third moving-object position data;
        generate display image data of the subject, the image data having a shape representing the calculated vector calculated using the first bubble tracking process including decimation processing;
        generate other display image data having a shape representing the calculated other vector calculated using the second bubble tracking process; and
        display, on a display, the results of the hybrid processing by displaying the display image data and the other display image data side by side.

2. The analysis apparatus according to claim 1, wherein the processing circuitry is further configured to:
    acquire an instruction relating to the display of the display image data or the other display image data; and
    display the display image data or the other display image data in accordance with the instruction.

3. The analysis apparatus according to claim 1, wherein the processing circuitry is further configured to:
compare a first correlation coefficient between the first moving-object position data and the second moving-object position data with a second correlation coefficient between the first moving-object position data and the third moving-object position data, and output an instruction relating to a display of the display image data or the other display image data corresponding to a higher correlation coefficient of the first correlation coefficient and the second correlation coefficient; and
display the display image data or the other display image data in accordance with the instruction.

4. The analysis apparatus according to claim 3, wherein the processing circuitry is further configured to:
calculate the first correlation coefficient of the first moving-object position data and the second moving-object position data, and calculate the second correlation coefficient of the first moving-object position data and the third moving-object position data.

5. The analysis apparatus according to claim 4, wherein the first correlation coefficient is calculated by using pattern matching between the first moving-object position data and the second moving-object position data, and the second correlation coefficient is calculated by using pattern matching between the first moving-object position data and the third moving-object position data.

6. The analysis apparatus according to claim 1, wherein the processing circuitry is further configured to calculate the vector without using a medical image corresponding to a frame between the first frame and the second frame.

7. The analysis apparatus according to claim 1, wherein a number of frames between the first frame and the second frame varies depending on a movement amount of the moving object.

8. The analysis apparatus according to claim 1, wherein the processing circuitry is further configured to calculate additional vectors from the medical images, and
the display image data has a plurality of shapes representing the additional vectors calculated by the processing circuitry.

9. An ultrasound diagnosis apparatus for presenting results of a hybrid processing including a first bubble tracking process including decimation processing and a second bubble tracking process using processing different from the decimation processing, the ultrasound diagnosis apparatus comprising
processing circuitry configured to
generate a plurality of ultrasound images respectively corresponding to a plurality of consecutive frames by transmission and reception of ultrasound waves;
generate first moving-object position data indicating a position of a moving object in a subject from a first ultrasound image of the plurality of ultrasound images, the first ultrasound image corresponding to a first frame, the moving object being a contrast agent bubble or a red blood cell;
generate second moving-object position data indicating a position of the moving object in the subject from a second ultrasound image of the plurality of ultrasound images, the second ultrasound image corresponding to a second frame that is two or more frames prior to the first frame;
generate third moving-object position data indicating a position of the moving object from a third ultrasound image of the plurality of ultrasound images, the third ultrasound image corresponding to a third frame that is prior to the first frame and subsequent to the second frame;
calculate a vector representing a movement of the moving object, using the first bubble tracking process including the decimation processing, based on only the first moving-object position data and the second moving-object position data;
calculate another vector representing a movement of the moving object, using the second bubble tracking process different from the first bubble tracking process, based on only the generated first moving-object position data and the generated third moving-object position data;
generate display image data having a shape representing the calculated vector calculated using the first bubble tracking process including decimation processing; and
generate other display image data having a shape representing the calculated other vector calculated using the second bubble tracking process; and
display, on a display, the results of the hybrid processing by displaying the display image data and the other display image data side by side.

10. An analysis apparatus for presenting results of a hybrid processing including a first bubble tracking process including decimation processing and a second bubble tracking process using processing different from the decimation processing, the analysis apparatus comprising:
processing circuitry configured to
acquire a plurality of medical images respectively corresponding to a plurality of consecutive frames, the medical images being obtained from a medical scan of a subject using a medical scanning apparatus;
generate first moving-object position data indicating a position of a moving object in the subject from a first medical image of the plurality of medical images, the first medical image corresponding to a first frame, the moving object being a contrast agent bubble or a red blood cell;
generate second moving-object position data indicating a position of the moving object in the subject from a second medical image of the plurality of medical images, the second medical image corresponding to a second frame that is two or more frames prior to the first frame;
generate third moving-object position data indicating a position of the moving object from a third medical image of the plurality of medical images, the third medical image corresponding to a third frame that is prior to the first frame and subsequent to the second frame;
calculate a vector representing a movement of the moving object, using the first bubble tracking process including the decimation processing, based on only the generated first moving-object position data and the generated second moving-object position data;
calculate another vector representing a movement of the moving object, using the second bubble tracking process different from the first bubble tracking process, based on only the generated first moving-object position data and the generated third moving-object position data;
generate display image data of the subject, the image data having a shape representing the calculated vector calculated using the first bubble tracking process including decimation processing;
generate other display image data having a shape representing the calculated other vector calculated using the second bubble tracking process;
superimpose the display image data and the other display image data to generate superimposed image data; and
display, on a display, the results of the hybrid processing by displaying the superimposed image data.

* * * * *